United States Patent
Iseli et al.

(10) Patent No.: US 10,426,663 B2
(45) Date of Patent: Oct. 1, 2019

(54) DEVICE FOR A MEDICAL TREATMENT OF A SCLERA

(71) Applicants: UNIVERSITÄT LEIPZIG, Leipzig (DE); Hans Peter Iseli, Geroldswil (CH)

(72) Inventors: Hans Peter Iseli, Geroldswil (CH); Mike Francke, Leipzig (DE); Peter Wiedemann, Leipzig (DE)

(73) Assignee: UNIVERSITÄT LEIPZIG, Leipzig (DE)

( * ) Notice: Subject to any disclaimer, the term of this patent is extended or adjusted under 35 U.S.C. 154(b) by 259 days.

(21) Appl. No.: 15/302,854

(22) PCT Filed: Apr. 2, 2015

(86) PCT No.: PCT/EP2015/057319
§ 371 (c)(1),
(2) Date: Oct. 7, 2016

(87) PCT Pub. No.: WO2015/155117
PCT Pub. Date: Oct. 15, 2015

(65) Prior Publication Data
US 2017/0087017 A1    Mar. 30, 2017

(51) Int. Cl.
*A61F 9/00* (2006.01)
*A61F 9/008* (2006.01)

(52) U.S. Cl.
CPC .......... *A61F 9/00821* (2013.01); *A61F 9/008* (2013.01); *A61F 9/0017* (2013.01);
(Continued)

(58) Field of Classification Search
CPC ..... A61F 9/00821; A61F 9/0017; A61F 9/008
See application file for complete search history.

(56) References Cited

U.S. PATENT DOCUMENTS

| 5,423,800 A | 6/1995 | Ren et al. |
| 5,688,264 A | 11/1997 | Ren et al. |

(Continued)

FOREIGN PATENT DOCUMENTS

| JP | 2011212115 A | 10/2011 |
| WO | 2001/028473 A1 | 4/2001 |

(Continued)

OTHER PUBLICATIONS

International Search Report and Written Opinion for International Application No. PCT/EP2015/057319, dated Jun. 11, 2015 (14 pages).

(Continued)

*Primary Examiner* — Edelmira Bosques
(74) *Attorney, Agent, or Firm* — Kagan Binder, PLLC

(57) ABSTRACT

The invention provides a device for a medical treatment of a sclera, the device comprising a single applicator connected to a shaft, wherein the applicator is configured to be placed into the Tenon's space; the applicator has a first surface, wherein the first surface of the applicator is superficially contactable to the surface of an area of the sclera so as to superficially cover said area; and the applicator comprises a single optical outlet connected to a single optical guiding element extending from a proximal end of the shaft to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation.

54 Claims, 18 Drawing Sheets

(52) U.S. Cl.
CPC .............. *A61F 2009/00853* (2013.01); *A61F 2009/00865* (2013.01)

(56) References Cited

U.S. PATENT DOCUMENTS

| | | |
|---|---|---|
| 2004/0093046 A1 | 5/2004 | Sand |
| 2005/0054900 A1 | 3/2005 | Mawn et al. |
| 2010/0189817 A1 | 7/2010 | Krueger et al. |
| 2012/0209051 A1 | 8/2012 | Blumenkranz et al. |
| 2012/0310141 A1 | 12/2012 | Kornfield et al. |

FOREIGN PATENT DOCUMENTS

| | | |
|---|---|---|
| WO | 2006/058189 A2 | 6/2006 |
| WO | 2014159691 A1 | 10/2014 |

OTHER PUBLICATIONS

Written Opinion for Singapore Application No. 11201608257R, dated Aug. 4, 2015 (6 pages).
Communication Pursuant to Article 94(3) EPC for European Application No. 15716003.7, dated Jul. 2, 2019 (6 pages).

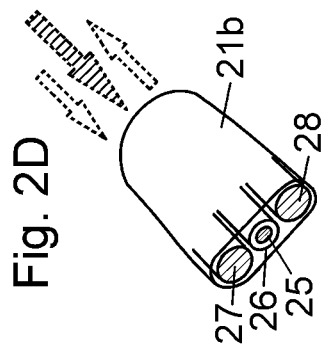
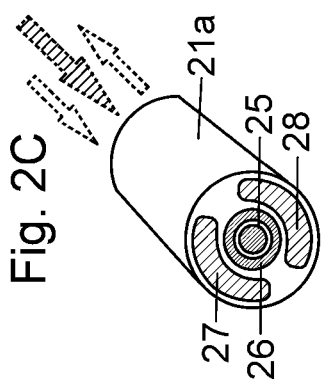
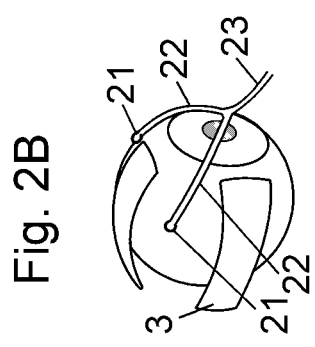
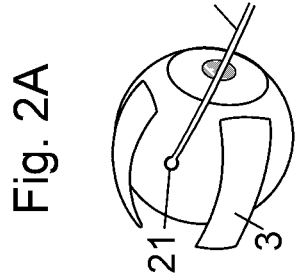

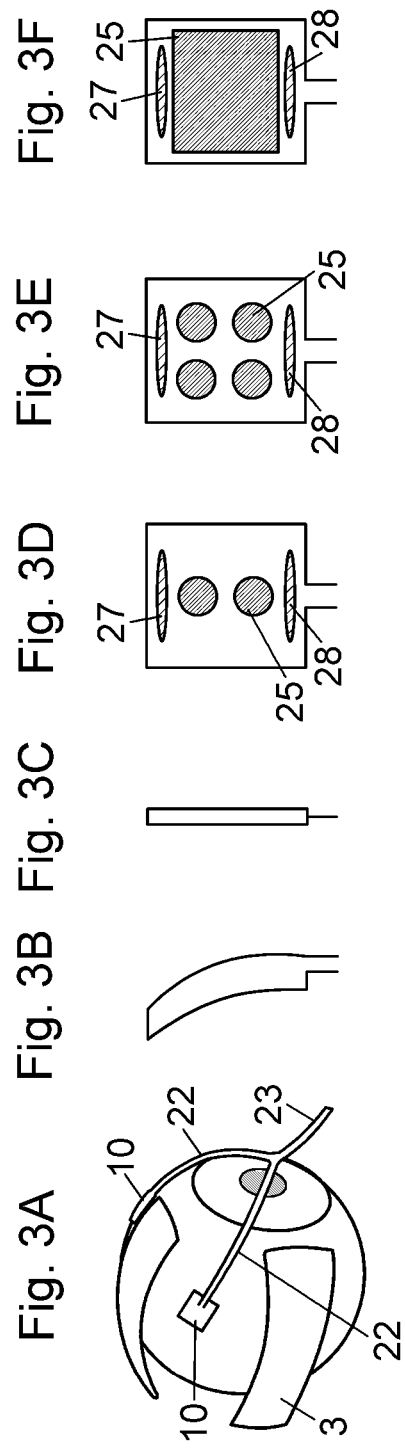

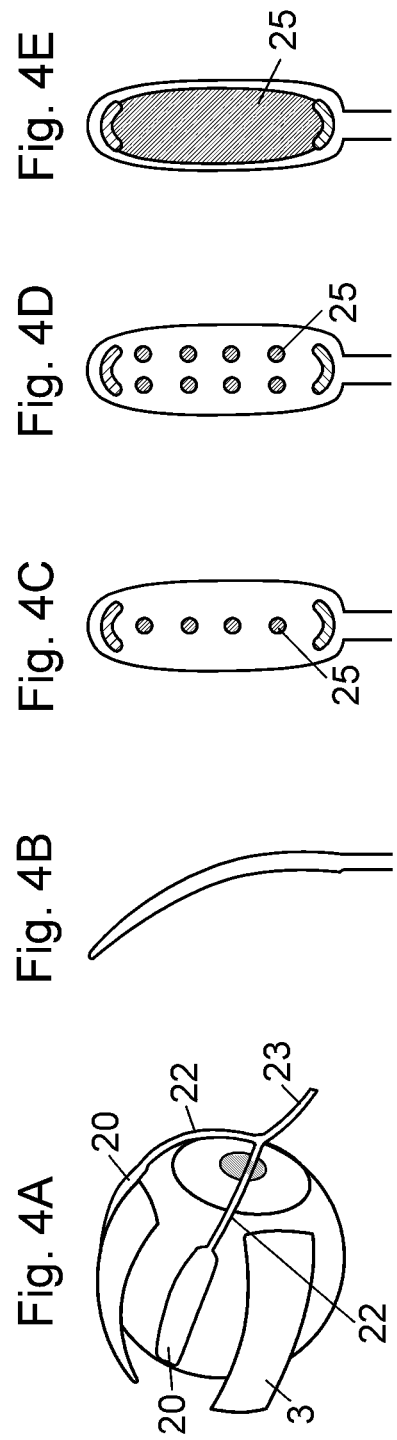

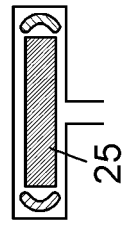
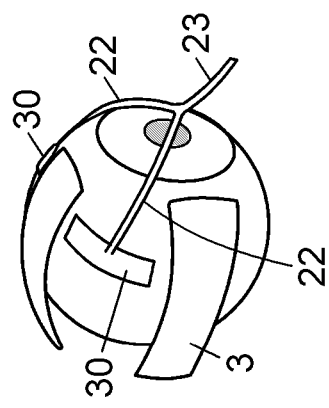

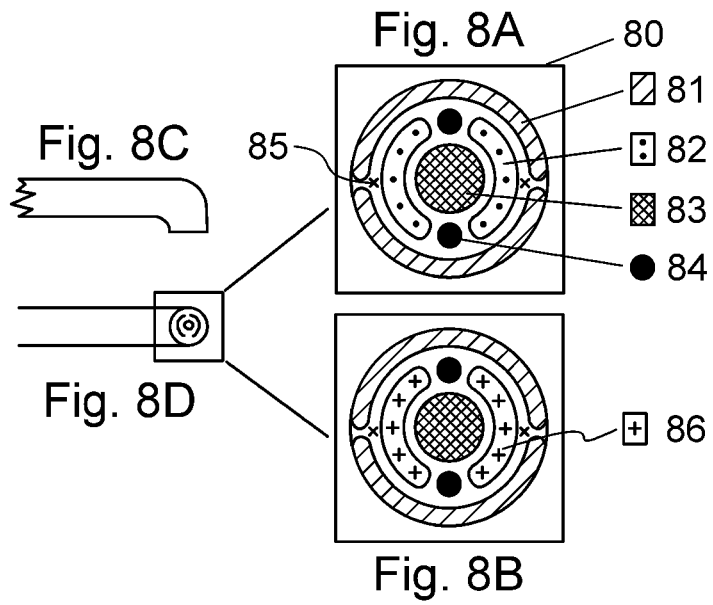
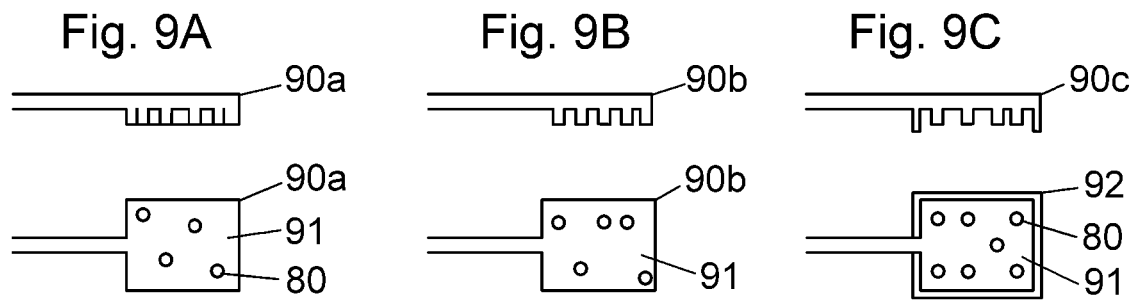
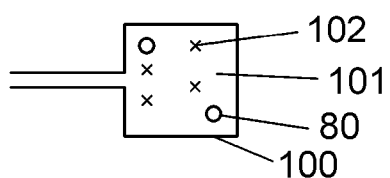

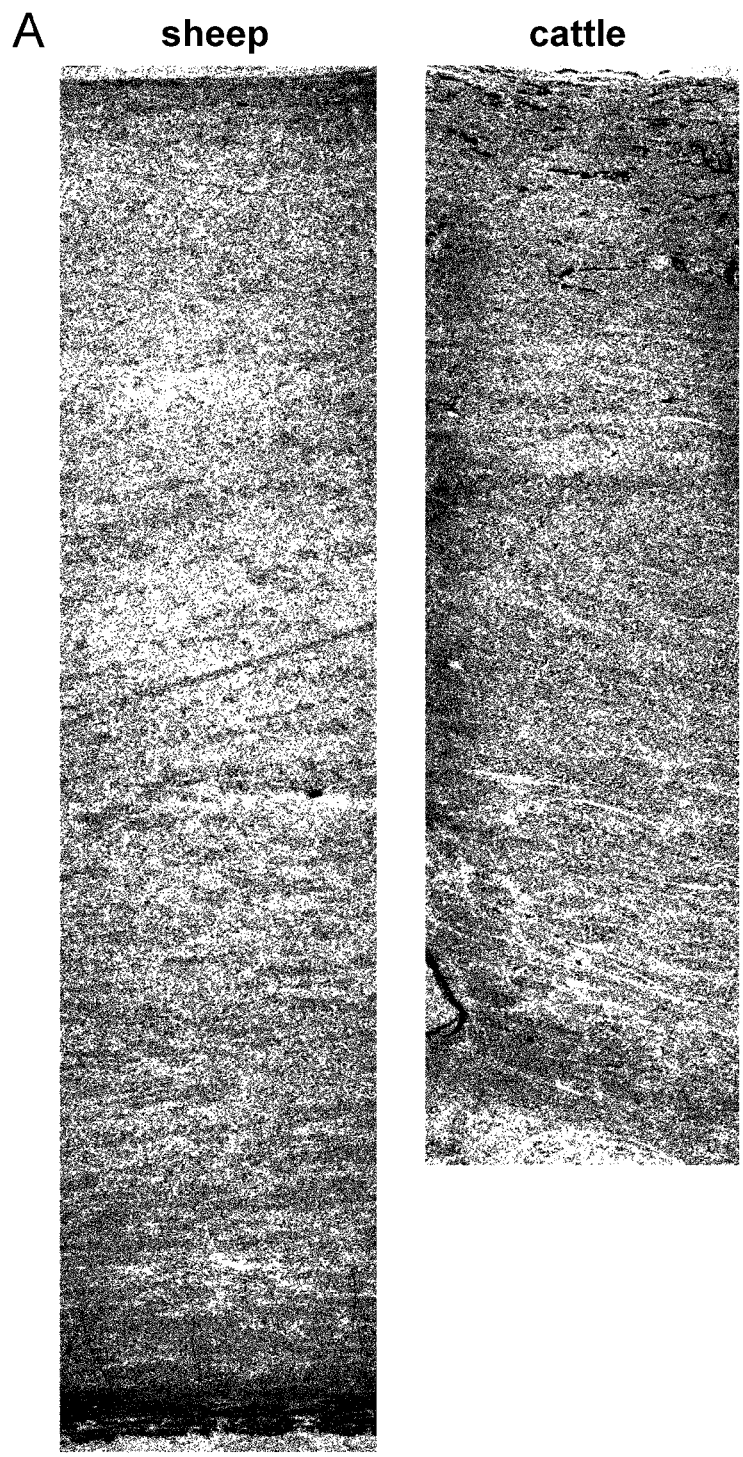
Fig. 14A (to be continued)

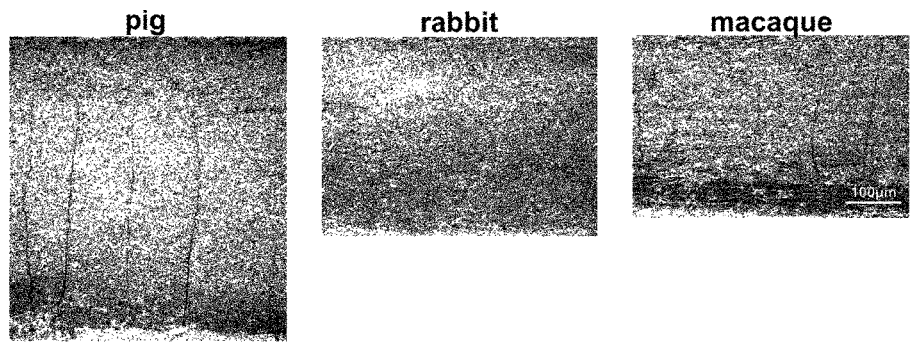
Continuation of Fig. 14A
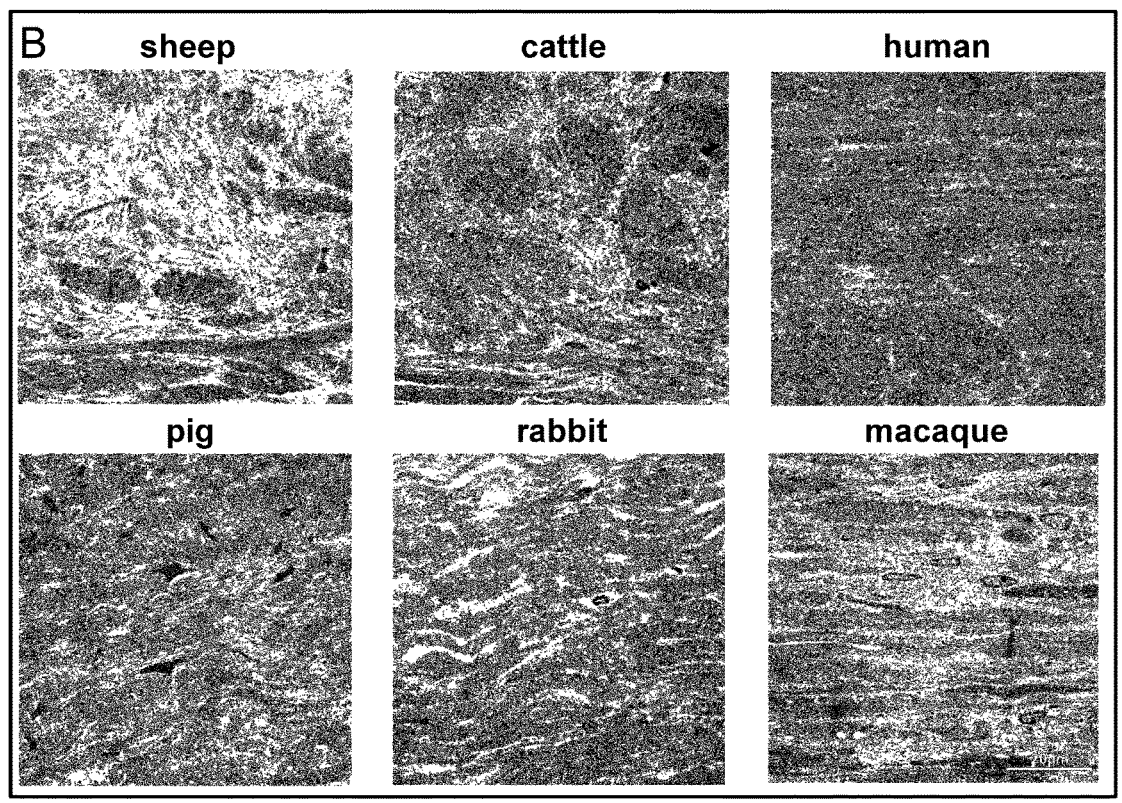
Fig. 14B

DEVICE FOR A MEDICAL TREATMENT OF A SCLERA

CROSS-REFERENCE TO RELATED APPLICATIONS

This application claims priority to International Application No. PCT/EP2015/057319, filed Apr. 2, 2015, and titled "A DEVICE FOR A MEDICAL TREATMENT OF A SCLERA", which in turn claims priority from European Application having Ser. No. 14/164,091.2, filed on Apr. 9, 2014, both of which are incorporated herein by reference in their entireties.

FIELD OF THE INVENTION

The present invention generally relates to a substance application and irradiation system (SAIS-Spot) for the locally defined and punctual treatment of the sclera-tissue of the eye. Thus, the invention relates to a medical device for substance application (and/or radiation) during ophthalmological surgical procedures on a patient. In particular, the invention relates to a device for medical treatment of a sclera.

BACKGROUND OF THE INVENTION

Collagen crosslinking (by applying riboflavin and UV-A light radiation) has been used in the past years in ophthalmology for the treatment of patients with maceration diseases of the cornea (the translucent part of the adventitia in the front part of the eye) (Wollensak et al., American Journal of Ophthalmology 2003, 135:620-627). The application of substances and light is significantly easier in the front part of the eye, since this part can be reached directly without surgical procedures.

Collagen crosslinking of the sclera for the treatment of progressive myopia (scleral crosslinking) is new and has so far only been tested in animal experiments (Iseli et al., Journal of Refractive Surgery 2008, 24:752-755; Wollensak et al., Acta Ophthalmologica Scandinavica 2005, 83: 477-482).

At this point in time there is no system for substance application or radiation for an extensive treatment of the outer part of the eye (especially the posterior and equatorial areas of the sclera) for the treatment of pathological deformation of the sclera. On the one hand, this therapeutic approach for the treatment of progressive myopia (scleral crosslinking through riboflavin and blue-light therapy) is completely new, and on the other hand, there are no therapeutic approaches for other diseases that would have required a substance application-/radiation system in ophthalmology.

In the inventor's experimental research, the photosensitive substance (riboflavin) was dripped into the Tenon's space and radiation ensued with a light application system (Bluephase 16i, Ivoclar Vivadent GmbH, Ellwangen-Jagst, Germany) which was designed for use in dentistry. For the use in our field, the inventors made several modifications (such as certain attachments to regulate the amount of light-energy). An extensive and homogenous radiation especially of the rear areas of the sclera is not possible with this auxiliary system. Substances have to be applied separately and alternating with radiation and will spread unevenly throughout the entire Tenon's space. This system is completely unsuitable for use in human eye surgery, since, inter alia, it cannot factor in the anatomy (size and shape of the human eye, muscle and nerve endings, vascular anatomy, etc).

Known instruments for substance application are designed for the localized application on the fibrous connective tissue directly on the sclera (episclera, sub-Tenon's space). Known patents describe a substance application under the episclera/sub-Tenon's space (WO 01/28473 A1, US 2010/0114039 A, WO 03/009784 A1) or they are meant for the localized application on the conjunctiva (WO 2010/105130 A2). These applications are aimed at small-scale, rather selective treatment of the retina; i.e. the sub-scleral tissue in the innermost part of the eye (see also FIG. 1). The substance thus has to first penetrate the outer tissue of the eye such as sclera and choroidea to reach its target location, the retina. The known systems only use the exterior application to the sclera to avoid the surgical application directly into the eye on the surface of the retina. These methods still bear the risk of post-surgical inflammation and injuries of the adventitia of the eye and are also not designed for the treatment of scleral tissue. The therapeutic aim of these treatment methods is thus a completely different one. The substance application and radiation system (SAIS-Spot) according to the present invention is applied directly to the site of the sclera that is to be treated in the Tenon's space (the space between the eye and the orbital cavity; see FIG. 1). The presently claimed system is positioned exactly where the treatment site is; i.e. the outer scleral tissue. Our approach does not involve any increased risk of complications during and after surgery vis-à-vis established surgical methods.

Applicators that have been described so far are used to form or release depots for medicine (WO 01/28473 A1, US 2010/0114039 A) and are not designed to release medicine/agents during surgical treatment and to then be removed again after surgery.

WO 03/009784 A1 suggests to implant a medication depot permanently into the sub-Tenon's space, it will thus not be removed at the end of surgery. As has already been mentioned, all of these applicators have the retina as primary target tissue. The present application is directed to the treatment of the sclera. None of the applicators is capable of covering the sclera sufficiently for treatment. All existing applicators have to be understood as local small-scale applicators, they affect a completely different target tissue and have different treatment approaches for different diseases. Additionally, all applicators cannot really regulate the substances application/delivery. Furthermore, none of these applicators can ensure an undesired diffusion of the substances and that adjacent tissues will not be affected by the treatment.

WO 2012/058382 A2 describes a device for delivering an active agent to target tissue at a site that includes a bodily fluid. The device includes a body having a first exterior surface including a first section having a local, discrete recessed area formed in the body for holding the active agent. The body includes a surface flow feature in the form of a canal that is formed in the body and is recessed relative to the exterior surface. The surface flow feature interfaces with the first section and the local recessed area and is configured so as to guide or modify flow of the bodily fluid relative to the body such that fluid communication is provided between the bodily fluid and the local recessed area. The local recessed area is recessed relative to at least a portion of the canal. The device can also be in the form of a device that has an erodible member that releases the active agent over a prescribed period of time.

WO 2006/058189 A2 provides a medical device having a thermistor for temperature measurement, irrigation/aspiration ports for fluid exchange and application of therapeutic modalities, a pressure manometer for pressure measurement, and an external system for control of temperature, pressure, and flow rate. When applied to the eye and orbit, this device can be used in hypothermia or hyperthermia applications, the control of intraocular pressure (IOP), and the application of treatment modalities. Methods of using the device in treating patients suffering from central retinal artery occlusion, anterior optic nerve disease, pathology of the choroid and retina including the macula, inflammation of the eye including the vitreous and anterior segment, glaucoma, inflammation and/or infections of the anterior and/or posterior segment of the eye, treatment before/during/after surgery of the eye, and the application of treatment modalities through a semipermeable membrane are described.

In WO 2008/011125 A2, devices, systems and techniques for delivering drugs to an ocular tissue are described. In at least some embodiments, a terminal component (e.g., a needle or open end of a catheter) is implanted in an ocular tissue and used to deliver one or more drugs. The delivered drugs may come from a source which is also implanted, or may be introduced from an external source (e.g., via a port). Both solid and liquid drug formulations can be used. Ocular implants can alternatively include a thin film coating that releases a drug into an ocular tissue.

U.S. Pat. No. 5,725,493 A discloses an intravitreal medicine delivery device and method including an implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be controlled, and the device is constructed so as to filter medicines delivered to the cavity and also avoids damage to or interference with other parts of the eye during implantation or during use.

WO 02/074196 A1 describes ocular implant devices for the delivery of a therapeutic agent to an eye in a controlled and sustained manner. Dual mode and single mode drug delivery devices are illustrated and described. Implants suitable for subconjunctival placement are described. Implants suitable for intravitreal placement also are described. The invention also includes fabrication and implementation techniques associated with the unique ocular implant devices that are presented herein.

US 2012/0209051 describes delivery systems and methods for delivering riboflavin (R/F) and UVA irradiation to the sclera. The R/F is delivered and then activated with UVA irradiation through the use of LEDs or optical fibers and separate cooling substance channels for the LEDs, thereby causing cross-linking of the collagen tissue. Delivery systems include implantable structures which provide surfaces that conform to the sclera. The delivery systems include various types of structures for delivery of R/F onto the sclera surface. Additionally, the delivery systems include UVA sources which provide irradiation of R/F in sclera collagen tissue.

None of the existing prior art describes the introduction of separate systems into the same application system (e.g. agent/substance and electromagnetic waves, or the application of different separate agents) which can be essential for the method of collagen crosslinking. None of the prior art allows for the control of a finely tuned localized medication release or a simultaneous dosing of the radiation. Suction systems for superfluous substances/agents are also not provided for in these applicators.

So far, there is no application system which is suitable for use on the sclera with the new treatment approach according to the invention. Existing substance applicators are designed for localized application of substances in cases when the tissue targeted for treatment is not the sclera but the underlying tissue (mostly the retina in the inner part of the eye). The presently claimed applicator can apply substances, electromagnetic waves, such as light, or heat extensively and in a controlled manner to all parts of the sclera, which has not been possible so far.

A shortcoming in the system that has so far been used in animal experiments is the size of the radiation unit in restricted spaces, which leads to severe or dangerous manipulation of the eye. An extensive and homogenous radiation also of the back parts of the sclera is not possible with this auxiliary system. Furthermore, the radiation system only radiates in certain predetermined time intervals. It is not possible to freely control the radiation energy levels. Since the only light power settings in the radiator employed by us were 50% or 100%, auxiliary plastic attachments had to be developed which enabled the use of graduated light power levels. Substances could only be applied by dripping them onto the tissue which leads to an inhomogeneous distribution of the substance. Thus, the substance also reaches tissue areas that are not supposed to be treated. Moreover, substance applicators and parallel systems (e.g. light) cannot be used simultaneously. There are no specially formed suction systems. So far, it is also not possible to extensively treat the middle and rear part of the eye/sclera.

The invention resolves disadvantages of the auxiliary system from the animal experiments and of other systems and treatment approaches respectively. Such disadvantages are:

anatomically unsuitable for extensive/comprehensive treatment of the sclera in view of the anatomy of the treated eye the locally or temporally parallel application of different substances is not possible a temporal and local combination of substance application and electromagnetic radiation (e.g. light) and/or electricity (monopolar and bipolar coagulation) is not possible; the necessary alternation between the application of substances and light leads to a considerable increase in the duration of surgery/treatment protein coagulation or the application of heat is not possible since substance and light applicators have to be attached and detached periodically alternating, the treatment becomes inhomogeneous because the surgeon has to constantly rearrange everything; moreover, the attaching and detaching bears an increased risk of damaging the surrounding tissue there is no return/suction system for superfluous substances, tissue not to be treated is always affected/co-treated there is no protection for radiation sensitive substances from the radiation until the radiation has arrived at the application-/treatment site (no shielding of the substance feeding exists)

known application systems cannot be introduced under visual control (video system)

known systems cannot supply a high light quantity to the sclera known systems cannot detect the contact between the applicator and the sclera So far, there is no application system that is suitable for use on the sclera or the treatment approach according to the invention. The therapeutic approach for the treatment of progressive myopia or pathological changes due to sclera maceration is completely new. Therefore, there is no surgical equipment that meets the requirements of this method of treatment or this surgical procedure. Individual technical methods for substance application or for the radiation of areas/tissue are always streamlined for their specific uses and do not fulfil the requirements of our therapeutic approach. There is a need for an extensive system for the homogeneous substance application and/or radiation that takes the exact anatomic structure of the eye into account and meets all the technical requirements of the treatment or the surgical procedure.

The disadvantages and shortcomings of the substance application and the radiation unit used in the animal experiments would also be eliminated by the new application system (SAIS-Spot).

SUMMARY OF THE INVENTION

In one aspect, the invention provides a device for a medical treatment of a sclera, the device comprising a single applicator connected to a shaft, wherein:
the applicator is configured to be placed into the Tenon's space;
the applicator has a first surface, wherein the first surface of the applicator is superficially contactable to the surface of an area of the sclera so as to superficially cover said area; and
the applicator comprises a single optical outlet connected to a single optical guiding element extending from a proximal end of the shaft to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation.

In one embodiment of the device, the distal surface of the optical outlet is at least partially coloured adapted for generating heat.

In one embodiment of the device, the applicator comprises a plurality of individual optical outlets connected to the single optical guiding element. The distal surface of at least one of the optical outlets may be coloured adapted for generating heat.

In one embodiment of the device, the optical outlets are regularly, irregularly or distinct distributed with respect to the first surface of the applicator, and the first surface of the applicator is preferably virtually subdivided into different areas having different distributions of the optical outlets. The density of the optical outlets may vary with respect to the first surface of the applicator.

In one embodiment of the device, the applicator has a symmetric shape, and the optical outlets are arranged symmetrically in accordance with the symmetry of the applicator.

In one embodiment of the device, the applicator comprises a single agent channel extending from a proximal end of the shaft to a distal channel opening at the surface of the applicator, the proximal end of the agent channel being connectable to an agent supply. The single agent channel may extend from a proximal end of the shaft to at least two distal channel openings at the first surface of the applicator. The applicator may further comprise a channel for sucking away superfluous agent.

In one embodiment of the device, the applicator comprises a plurality of agent channels. Each agent channel may extend from a proximal end of the shaft to at least two distal channel openings at the first surface of the applicator. In one embodiment, the one or more agent channels are for the application of an agent such as riboflavin, whereas one or more of the remaining channels are for sucking away superfluous agent.

In one embodiment of the device, the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device, the surface of the applicator has a structure adapted to allow for an improved distribution of agent when agent is lead through the agent channel. The surface structure may comprises chamfers, or elements such as bars, half-spheres, pyramids or cones.

In one embodiment of the device, the applicator further comprises a single optical outlet connected to a single optical guiding element extending from a proximal end of the shaft to the single distal optical outlet at the first surface of the applicator, the optical guiding element being configured for guiding electromagnetic waves configured for crosslinking sclera tissue towards the optical outlet. The applicator may comprise a plurality of individual optical surface areas connected to the optical guiding element.

In one embodiment of the device, the applicator comprises a plurality of individual first optical surface areas connected to a first optical guiding element and a plurality of individual second optical surface areas connected to a second optical guiding element, the first and second optical guiding element extending from a proximal end of the shaft to the respective distal optical surface areas at the first surface of the applicator, the first optical guiding element being configured for guiding electromagnetic waves towards the optical first optical surface areas, and the second guiding element being associated with a photosensitizer.

In one embodiment of the device, the applicator further comprises a single monopolar or bipolar electrode connected to a single electrical conductor element extending from a proximal end of the shaft to the electrode at the first surface of the applicator.

In one embodiment of the device, the applicator further comprises multiple monopolar or bipolar electrodes connected to multiple electrical conductor elements extending from a proximal end of the shaft to the electrodes at the first surface of the applicator. The electrodes may provide electrical protein coagulation at a spot.

In one aspect, the invention provides a device for a medical treatment of a sclera, the device comprising two, three, four or more applicators each connected to a respective shaft, wherein:
each applicator is configured to be placed into the Tenon's space;
each applicator has a first surface, wherein the first surface of the applicator is superficially contactable to the surface of an area of the sclera so as to superficially cover said area;

each applicator comprises a single optical outlet connected to a single optical guiding element extending from a proximal end of the respective shaft to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation; and wherein the shafts of the applicators are proximally connected to a single proximal shaft.

In one embodiment of the device, the distal surface of the optical outlet is at least partially coloured adapted for generating heat.

In one embodiment of the device, each applicator comprises a plurality of individual optical outlets connected to the single optical guiding element. The distal surface of at least one of the optical outlets may be coloured adapted for generating heat. The optical outlets may be regularly, irregularly or distinct distributed with respect to the first surface of the applicator, and the first surface of the applicator is preferably virtually subdivided into different areas having different distributions of the optical outlets. The density of the optical outlets may vary with respect to the first surface of the applicator. The applicator may have a symmetric shape, and the optical outlets are arranged symmetrically in accordance with the symmetry of the applicator.

In one embodiment of the device, each applicator comprises a single agent channel extending from a proximal end of the shaft to a distal channel opening at the surface of the applicator, the proximal end of the agent channel being connectable to an agent supply. The single agent channel may extend from a proximal end of the shaft to at least two distal channel openings at the first surface of the applicator. Each applicator may further comprise a channel for sucking away superfluous agent. Each applicator may comprise a plurality of agent channels. Each agent channel may extend from a proximal end of the shaft to at least two distal channel openings at the first surface of the applicator.

In one embodiment of the device, the one or more agent channels are for the application of an agent such as riboflavin, whereas one or more of the remaining channels are for sucking away superfluous agent.

In one embodiment of the device, the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device, the surface of each applicator has a structure adapted to allow for an improved distribution of agent when agent is lead through the agent channel. The surface structure may comprise chamfers, or elements such as bars, half-spheres, pyramids or cones.

Each applicator may further comprise a single optical outlet connected to a single optical guiding element extending from a proximal end of the shaft to the single distal optical outlet at the first surface of the applicator, the optical guiding element being configured for guiding electromagnetic waves configured for crosslinking sclera tissue towards the optical outlet. Each applicator may comprise a plurality of individual optical surface areas connected to the optical guiding element.

In one embodiment of the device, each applicator comprises a plurality of individual first optical surface areas connected to a first optical guiding element and a plurality of individual second optical surface areas connected to a second optical guiding element, the first and second optical guiding element extending from a proximal end of the shaft to the respective distal optical surface areas at the first surface of the applicator, the first optical guiding element being configured for guiding electromagnetic waves towards the optical first optical surface areas, and the second guiding element being associated with a photosensitizer.

In one embodiment of the device, each applicator further comprises a single monopolar or bipolar electrode connected to a single electrical conductor element extending from a proximal end of the shaft to the electrode at the first surface of the applicator.

In one embodiment of the device, each applicator further comprises multiple monopolar or bipolar electrodes connected to multiple electrical conductor elements extending from a proximal end of the shaft to the electrodes at the first surface of the applicator.

In one embodiment of the device, the electrodes provide electrical protein coagulation at a spot.

In one embodiment of the device, the device further comprises a shield element sized and shaped to at least partially cover the cornea during use of the device.

In one embodiment of the device, the device comprises one or more recesses are formed in the edge of the applicator. The one or more recesses may be positioned and formed such that the recesses leave free space for eye muscles, blood vessels and/or nerves when the applicator is positioned on said area of the sclera.

In one embodiment of the device, the applicator comprises a base layer made from a material preferably being at least one of sterilisable and heat-resistant, for example medical steel or plastic, and is preferably impervious to light.

In one embodiment of the device, the applicator comprises one or more additional layers, wherein the base layer and the one or more additional layers are arranged as stacked layers with the base layer on the outer side of the applicator so as to support the additional layers, and wherein each of the one or more additional layers is preferably made from a plastic or a metal material, more preferably light-diffusing, light blocking and/or sponge like material. The at least one of the additional layers may be a diffuser adapted for diffusing electromagnetic waves, and wherein at least part of the distal openings are arranged within or at the outer side of the additional layer(s) being a diffuser.

In one aspect, the invention provides a method of treating the sclera in a subject comprising the steps of
(i) placing of the applicator of the device of any of the preceding claims into the Tenon's space in the eye of the subject so that the first surface of the applicator is superficially in contact with a surface of an area of the sclera,
(ii) applying electromagnetic radiation to the sclera of the subject of a wavelength adapted for thermal treatment of the sclera by protein coagulation.

The method may comprise the step of applying riboflavin to the sclera for crosslinking.

The method may comprise applying electrical protein coagulation at a spot.

One aspect of the invention relates to a device for a medical treatment of a sclera, the device comprising a single applicator connected to a shaft, wherein:
the applicator is configured to be placed into the Tenon's space;

the applicator has a surface, wherein the surface of the applicator is superficially contactable to the surface of an area of the sclera so as to superficially cover said area; and the applicator and shaft comprises a single agent channel extending from a proximal end of the shaft to a single distal opening at the first surface of the applicator, the proximal end of the agent channel being connectable to an agent supply.

In one embodiment of the device the single opening of the agent channel provides a local spot for treatment of the sclera.

In one embodiment of the device the agent channel is at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

The applicator may further comprise a channel that may be used for sucking away superfluous agent.

According to another aspect, the invention provides a device for a medical treatment of a sclera, the device comprising a single applicator connected to a shaft, wherein:
the applicator is configured to be placed into the Tenon's space;
the applicator has a surface, wherein the surface of the applicator is superficially contactable to the surface of an area of the sclera so as to superficially cover said area; and
the applicator comprises a single optical surface area connected to two guiding elements extending from a proximal end of the shaft to the single distal optical surface area at the surface of the applicator, one optical guiding element being configured for guiding electromagnetic waves towards the optical surface element, and the other guiding element being associated with a photosensitizer.

The single distal optical surface area may be at least partially coloured adapted for generating heat. Due to the just partial or semi-transparent colouring, light that is not absorbed by the colouring but passes can be used for crosslinking.

The applicator may further comprise a single monopolar electrode connected to a electrical conductor element extending from a proximal end of the shaft to the distal electrode at the first surface of the applicator, or bipolar electrodes connected to electrical conductor elements extending from a proximal end of the shaft to the distal electrodes at the first surface of the applicator. This may provide electrical protein coagulation at spot.

The applicator may further comprise a channel that may be used for sucking away superfluous agent.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising a single applicator connected to a shaft, wherein:

the applicator is configured to be placed into the Tenon's space;
the applicator has a first surface, wherein the first surface of the applicator is superficially contactable to the surface of an area of the sclera so as to superficially cover said area; and
the applicator comprises a single optical outlet connected to a single optical guiding element extending from a proximal end of the shaft to the single distal optical outlet at the first surface of the applicator, the optical guiding element being configured for guiding electromagnetic waves towards the optical outlet.

The optical guiding element is preferably configured to guide electromagnetic waves of a wavelength adapted for thermal treatment of the sclera.

The distal surface of the optical outlet may be at least partially coloured adapted for generating heat, i.e., in a manner that heat is generated by colour absorbed wavelengths and crosslinking is possible with transmitting light.

The applicator of this embodiment may comprise a single agent channel extending from a proximal end of the shaft to a distal channel opening at the surface of the applicator, the proximal end of the agent channel being connectable to an agent supply.

The applicator may further comprise a channel that may be used for sucking away superfluous agent.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising a single applicator connected to a shaft, wherein:
the applicator is configured to be placed into the Tenon's space;
the applicator has a surface, wherein the surface of the applicator is superficially contactable to the surface of an area of the sclera so as to superficially cover said area; and
the applicator comprises a single monopolar electrode connected to a electrical conductor element extending from a proximal end of the shaft to the single distal electrode at the first surface of the applicator, or bipolar electrodes connected to electrical conductor elements extending from a proximal end of the shaft to the distal electrodes at the first surface of the applicator.

According to another aspect, the invention provides a device for a medical treatment of a sclera, the device comprising a single flat applicator connected to a shaft, wherein:
the applicator is configured to be placed into the Tenon's space;
the applicator has a surface, wherein the surface of the applicator is superficially contactable to the surface of an area of the sclera so as to superficially cover said area; and
the applicator comprises a single agent channel extending from a proximal end of the shaft to at least two distal channel openings at the first surface of the applicator, the proximal end of the agent channel being connectable to an agent supply.

The agent channel may be at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

The surface of the applicator may have a structure adapted to allow for an improved distribution of agent when agent is lead through the agent channel, and wherein the surface structure can comprise chamfers, or elements such as bars, half-spheres, pyramids or cones.

The applicator may further comprise a channel that may be used for sucking away superfluous agent.

According to another aspect, the invention provides a device for a medical treatment of a sclera, the device comprising a single applicator connected to a shaft, wherein:
the applicator is configured to be placed into the Tenon's space;
the applicator has a first surface, wherein the first surface of the applicator is superficially contactable to the surface of an area of the sclera so as to superficially cover said area; and
the applicator comprises a first optical surface area connected to a first optical guiding element and a second optical surface area connected to a second guiding element, the first and second guiding element extending from a proximal end of the shaft to the respective distal optical surface area at the first surface of the applicator, the first optical guiding element being configured for guiding electromagnetic waves towards the optical surface area, and the second guiding element being associated with a photosensitizer.

The first optical surface area may be at least partially coloured adapted for generating heat. Due to the just partial colouring, light that is not absorbed by the colouring but passes can be used for crosslinking.

The applicator may further comprise a single monopolar electrode connected to a electrical conductor element extending from a proximal end of the shaft to the distal electrode at the first surface of the applicator, or bipolar electrodes connected to electrical conductor elements extending from a proximal end of the shaft to the distal electrodes at the first surface of the applicator. This may provide electrical protein coagulation by crosslinking at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used in this preferred embodiment for the application of an agent such as riboflavin, whereas one or more of the remaining channels may be used for sucking away superfluous agent.

According to another aspect, the invention provides a device for a medical treatment of a sclera, the device comprising a single applicator connected to a shaft, wherein:
the applicator is configured to be placed into the Tenon's space;
the applicator has a first surface and an opposite second surface, wherein the first surface of the applicator is superficially contactable to the surface of an area of the sclera so as to superficially cover said area; and
the applicator comprises a plurality of individual first optical surface areas connected to a first optical guiding element and a plurality of individual second optical surface areas connected to a second guiding element, the first and second optical guiding element extending from a proximal end of the shaft to the respective distal optical surface areas at the first surface of the applicator, the first optical guiding element being configured for guiding electromagnetic waves towards the optical first optical surface areas, and the second guiding element being associated with a photosensitizer.

The distal surface of at least one of the first optical surface areas is at least partially coloured adapted for generating heat. Due to the just partial or semi-transparent colouring, light that is not absorbed by the colouring but passes can be used for crosslinking.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising a single applicator connected to a shaft, wherein:
the applicator is configured to be placed into the Tenon's space;
the applicator has a first surface and an opposite second surface, wherein the first surface of the applicator is superficially contactable to the surface of an area of the sclera so as to superficially cover said area; and
the applicator comprises a plurality of individual optical outlets connected to a single optical guiding element extending from a proximal end of the shaft to the distal optical outlets at the first surface of the applicator, the optical guiding element being configured for guiding electromagnetic waves towards the optical outlet, wherein the optical guiding element is configured to guide electromagnetic waves of a wavelength adapted for thermal treatment of the sclera.

The optical outlets may be regularly, irregularly or distinct distributed with respect to the first surface of the applicator, and the first surface of the applicator can be virtually subdivided into different areas having different distributions of the optical outlets.

The density of the optical outlets may vary with respect to the first surface of the applicator.

The applicator may have a symmetric shape, and the optical outlets are preferably arranged symmetrically in accordance with the symmetry of the applicator.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising a single applicator connected to a shaft, wherein:
the applicator is configured to be placed into the Tenon's space;
the applicator has a first surface and an opposite second surface, wherein the first surface of the applicator is superficially contactable to the surface of an area of the sclera so as to superficially cover said area; and
the applicator comprises a plurality of individual optical outlets connected to a single optical guiding element extending from a proximal end of the shaft to the distal optical outlets at the first surface of the applicator, the optical guiding element being configured for guiding electromagnetic waves towards the optical outlet, wherein the distal surface of at least one of the optical outlets is coloured adapted for generating heat.

The optical outlets may be regularly, irregularly or distinct distributed with respect to the first surface of the applicator, and the first surface of the applicator can be virtually subdivided into different areas having different distributions of the optical outlets.

The density of the optical outlets may vary with respect to the first surface of the applicator.

The applicator may have a symmetric shape, and the optical outlets are preferably arranged symmetrically in accordance with the symmetry of the applicator.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation at a spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used is used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising a single applicator connected to a shaft, wherein:
the applicator is configured to be placed into the Tenon's space;
the applicator has a first surface and an opposite second surface, wherein the first surface of the applicator is superficially contactable to the surface of an area of the sclera so as to superficially cover said area; and
the applicator comprises at least two electrodes connected to a single electrical conductor element extending from a proximal end of the shaft to the at last two distal electrodes at the first surface of the applicator.

The electrodes may provide electrical protein coagulation at spot. The electrodes may be a monopolar or a bipolar electrode.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used in this preferred embodiment for the application of an agent such as riboflavin, whereas one or more of the remaining channels may be used for sucking away superfluous agent.

According to another aspect, the invention provides a device for a medical treatment of a sclera, the device comprising a two, three, four or more applicators each connected to a respective shaft, wherein:
each applicator is configured to be placed into the Tenon's space;
each applicator has a first surface, wherein the first surface of each applicator is superficially contactable to the surface of an area of the sclera so as to superficially cover said area;
each applicator and shaft comprises a single agent channel extending from a proximal end of the shaft to a single distal opening at the first surface of the applicator, the proximal end of the agent channel being connectable to an agent supply; and
wherein the shafts of the applicators are proximally connected to a single proximal supply shaft.

In one embodiment of the device the single opening of the agent channel provides a local spot for treatment of the sclera.

In one embodiment of the device the agent channel is at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

The applicator may further comprise a channel that may be used for sucking away superfluous agent.

According to another aspect, the invention provides a device for a medical treatment of a sclera, the device comprising two, three, four or more applicators each connected to a respective shaft, wherein:
- each applicator is configured to be placed into the Tenon's space;
- each applicator has a first surface, wherein the first surface of each applicator is superficially contactable to the surface of an area of the sclera so as to superficially cover said area;
- each applicator comprises a single optical surface area connected to two guiding elements extending from a proximal end of the respective shaft to the single distal optical surface area at the first surface of the applicator, one optical guiding element being configured for guiding electromagnetic waves towards the optical surface element, and the other guiding element being associated with a photosenistizer; and
- wherein the shafts of the applicators are proximally connected to a single proximal shaft.

The single distal optical surface area may be at least partially coloured adapted for generating heat. Due to the just partial colouring, light that is not absorbed by the colouring but passes can be used for crosslinking.

The applicator may further comprise a single monopolar electrode connected to a single electrical conductor element extending from a proximal end of the shaft to the single distal electrode at the first surface of the applicator, or bipolar electrodes connected to electrical conductor elements extending from a proximal end of the shaft to the distal electrodes at the first surface of the applicator. This may provide electrical protein coagulation at a spot.

The applicator may further comprise a channel that may be used for sucking away superfluous agent.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising two, three, four or more applicators each connected to a respective shaft, wherein:
- each applicator is configured to be placed into the Tenon's space;
- each applicator has a first surface, wherein the first surface of the applicator is superficially contactable to the surface of an area of the sclera so as to superficially cover said area;
- each applicator comprises a single optical outlet connected to a single optical guiding element extending from a proximal end of the respective shaft to the single distal optical outlet at the first surface of the applicator, the optical guiding element being configured for guiding electromagnetic waves towards the optical outlet; and
- wherein the shafts of the applicators are proximally connected to a single proximal shaft.

The optical guiding element may be configured to guide electromagnetic waves of a wavelength adapted for thermal treatment of the sclera.

The distal surface of the optical outlet may be at least partially coloured adapted for generating heat, i.e., in a manner that heat is generated by colour absorbed wavelengths and crosslinking is possible with transmitting light.

The applicator of this embodiment may comprise a single agent channel extending from a proximal end of the shaft to a distal channel opening at the surface of the applicator, the proximal end of the agent channel being connectable to an agent supply.

The applicator may further comprise a channel that may be used for sucking away superfluous agent.

In one embodiment of the device the surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising two, three, four or more applicators each connected to a respective shaft, wherein:
- each applicator is configured to be placed into the Tenon's space;
- each applicator has a first surface, wherein the first surface of the applicator is superficially contactable to the surface of an area of the sclera so as to superficially cover said area;
- each applicator comprises a single monopolar electrode connected to a electrical conductor element extending from a proximal end of the shaft to the single distal electrode at the first surface of the applicator, or bipolar electrodes connected to electrical conductor elements extending from a proximal end of the shaft to the distal electrodes at the first surface of the applicator; and
- wherein the shafts of the applicators are proximally connected to a single proximal shaft.

The electrode may provide electrical protein coagulation at a spot. The electrode may be a monopolar or a bipolar electrode.

According to another aspect, the invention provides a device for a medical treatment of a sclera, the device comprising two, three, four or more applicators each connected to a respective shaft, wherein:
- each applicator is configured to be placed into the Tenon's space;
- each applicator has a first surface, wherein first surface of the applicator is superficially contactable to the surface of an area of the sclera so as to superficially cover said area;
- each applicator comprises a single agent channel extending from a proximal end of the respective shaft to at least two distal channel openings at the first surface of the applicator, the proximal end of the agent channel being connectable to an agent supply; and
- wherein the shafts of the applicators are proximally connected to a single proximal agent supply shaft.

The agent channel may be at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

The first surface of the applicator may have a structure adapted to allow for an improved distribution of agent when agent is lead through the agent channel, and wherein the surface structure can comprise chamfers, or elements such as bars, half-spheres, pyramids or cones.

The distal channel openings may be regularly, irregularly or distinct distributed with respect to the first surface of the applicator, wherein the first surface of the applicator can be virtually subdivided into different areas having different distributions of the openings.

The density of the distal channel openings may be variable with respect to the first surface of the applicator.

The applicator may have a symmetric shape, and the distal channel openings are preferably arranged symmetrically in accordance with the symmetry of the applicator.

The agent channel may be at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

The first surface of the applicator may have a structure adapted to allow for an improved distribution of agent when agent is lead through the agent channel, and the surface structure can comprise chamfers, or elements such as bars, half-spheres, pyramids or cones.

The applicator may further comprise a channel that may be used for sucking away superfluous agent.

According to another aspect, the invention provides a device for a medical treatment of a sclera, the device comprising two, three, four or more applicators each connected to a respective shaft, wherein:

each applicator is configured to be placed into the Tenon's space;

each applicator has a first surface, wherein the first surface of the applicator is superficially contactable to the surface of an area of the sclera so as to superficially cover said area;

each applicator comprises a first optical surface area connected to a first optical guiding element and a second optical surface area connected to a second guiding element, the first and second guiding element extending from a proximal end of the respective shaft to the respective distal optical surface area at the first surface of the applicator, the first optical guiding element being configured for guiding electromagnetic waves towards the optical surface area, and the second guiding element being associated with a photosensitizer; and wherein the shafts of the applicators are proximally connected to a single proximal shaft.

The first distal optical surface area may be at least partially coloured adapted for generating heat. Due to the just partial colouring, light that is not absorbed by the colouring but passes can be used for crosslinking.

The applicator may further comprise a single monopolar electrode connected to a single electrical conductor element extending from a proximal end of the shaft to the single distal electrode at the first surface of the applicator, or bipolar electrodes connected to electrical conductor elements extending from a proximal end of the shaft to the distal electrodes at the first surface of the applicator. This may provide electrical protein coagulation by crosslinking at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used is used in this preferred embodiment for the application of an agent such as riboflavin, whereas one or more of the remaining channels may be used for sucking away superfluous agent.

According to another aspect, the invention provides a device for a medical treatment of a sclera, the device comprising two, three, four or more applicators each connected to a respective shaft, wherein:

each applicator is configured to be placed into the Tenon's space;

each applicator has a first surface, wherein the first surface of the applicator is superficially contactable to the surface of an area of the sclera so as to superficially cover said area;

each applicator comprises a plurality of individual first optical surface areas connected to a first optical guiding element and a plurality of individual second optical surface areas connected to a second guiding element, the first and second optical guiding element extending from a proximal end of the respective shaft to the respective distal optical surface areas at the first surface of the applicator, the first optical guiding element being configured for guiding electromagnetic waves towards the optical first optical surface areas, and the second guiding element being associated with a photosensitizer; and wherein the shafts of the applicators are proximally connected to a single proximal shaft.

The distal surface of at least one of the first optical surface areas is at least partially coloured adapted for generating heat. Due to the just partial or semi-transparent colouring, light that is not absorbed by the colouring but passes can be used for crosslinking.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation by crosslinking at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used is used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising two, three, four or more applicators each connected to a respective shaft, wherein:

each applicator is configured to be placed into the Tenon's space;

each applicator has a first surface, wherein the first surface of the applicator is superficially contactable to the surface of an area of the sclera so as to superficially cover said area;

each applicator comprises a plurality of individual optical outlets connected to a single optical guiding element extending from a proximal end of the respective shaft to the distal optical outlets at the first surface of the applicator, the optical guiding element being configured for guiding electromagnetic waves towards the optical outlet, wherein the optical guiding element is configured to guide electromagnetic waves of a wavelength adapted for thermal treatment of the sclera; and wherein the shafts of the applicators are proximally connected to a single proximal shaft.

The optical outlets may be regularly, irregularly or distinct distributed with respect to the first surface of the applicator, and the first surface of the applicator can be virtually subdivided into different areas having different distributions of the optical outlets.

The density of the optical outlets may vary with respect to the first surface of the applicator.

The applicator may have a symmetric shape, and the optical outlets are preferably arranged symmetrically in accordance with the symmetry of the applicator.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation by crosslinking at spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used is used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising two, three, four or more applicators each connected to a respective shaft, wherein:

each applicator is configured to be placed into the Tenon's space;

each applicator has a first surface and an opposite second surface, wherein the first surface of the applicator is superficially contactable to the surface of an area of the sclera so as to superficially cover said area;

each applicator comprises a plurality of individual optical outlets connected to a single optical guiding element extending from a proximal end of the respective shaft to the distal optical outlets at the first surface of the applicator, the optical guiding element being configured for guiding electromagnetic waves towards the optical outlet, wherein the distal surface of at least one of the optical outlets is coloured adapted for generating heat; and wherein the shafts of the applicators are proximally connected to a single proximal shaft.

The optical outlets may be regularly, irregularly or distinct distributed with respect to the first surface of the applicator, and the first surface of the applicator can be virtually subdivided into different areas having different distributions of the optical outlets.

The density of the optical outlets may vary with respect to the first surface of the applicator.

The applicator may have a symmetric shape, and the optical outlets are preferably arranged symmetrically in accordance with the symmetry of the applicator.

The applicator may further comprise a single or multiple monopolar or bipolar electrode(s) connected to a single (or multiple) electrical conductor element extending from a proximal end of the shaft to the electrode(s) at the first surface of the applicator. This may provide electrical protein coagulation at a spot.

The applicator may also comprise a single agent channel extending from a proximal end of the shaft to a single distal opening at the first surface of the applicator, the proximal end of the agent channel being connectable to an agent supply.

Additionally, a plurality of agent channels may be provided. One or more agent channels may be used is used in this preferred embodiment for the application of an agent such as riboflavin, whereas one or more of the remaining channels may be used for sucking away superfluous agent.

In one embodiment of the device the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

In one embodiment of the device the first surface of the applicator has a structure adapted to allow for an improved distribution of agent when agent is lead through the agent channel, and wherein the surface structure can comprise chamfers, or elements such as bars, half-spheres, pyramids or cones.

According to another aspect, the invention provides a device for a medical treatment of a sclera, the device comprising two, three, four or more applicators each connected to a respective shaft, wherein:

each applicator is configured to be placed into the Tenon's space;

each applicator has a first surface and an opposite second surface, wherein the first surface of the applicator is superficially contactable to the surface of an area of the sclera so as to superficially cover said area;

each applicator comprises at least two electrodes connected to a single electrical conductor element extending from a proximal end of the respective shaft to the at last two distal electrodes at the first surface of the applicator; and wherein the shafts of the applicators are proximally connected to a single proximal shaft.

The electrodes may provide electrical protein coagulation at a spot. The electrodes may be a monopolar or a bipolar electrode.

The device of the invention according to any embodiment may further comprise a shield element sized and shaped to at least partially cover the cornea during use of the device.

The applicator according to any embodiment may have a length between 2 mm and 30 mm, preferably a length between 5 mm and 25 mm, or more preferably a length of 15 mm.

The applicator according to any embodiment may have a width between 2 mm and 25 mm, preferably between 5 mm and 20 mm, or more preferably between 10 mm and 15 mm.

The thickness of the applicator according to any embodiment may be lower than or equal to 5 mm, or preferably lower than or equal to 3 mm, and has preferably a minimum of 2 mm.

According to according to any embodiment, one or more recesses are formed in the edge of the applicator. The one or more recesses may be positioned and formed such that the recesses leave free space for eye muscles, blood vessels and/or nerves when the applicator is positioned on said area of the sclera.

The applicator according to any embodiment may comprise a base layer made from a material preferably being at least one of sterilisable and heat-resistant, for example medical steel or plastic, and is preferably impervious to light.

In one embodiment, at least one of the outer surface of the applicator and the edge of the applicator is impervious to light.

In one embodiment the applicator comprises one or more additional layers, wherein the base layer and the one or more additional layers are arranged as stacked layers with the base layer on the outer side of the applicator so as to support the additional layers, and wherein each of the one or more additional layers is preferably made from a plastic or a metal material, more preferably light-diffusing, light blocking and/or sponge like material.

In one embodiment at least one of the additional layers is a diffuser adapted for diffusing electromagnetic waves, and wherein at least part of the distal openings are arranged within or at the outer side of the additional layer(s) being a diffuser.

In one embodiment a handle is arranged at the edge of the applicator. The handle may be connected to the single proximal shaft and is arranged as a tube and the first channel of each of the channel systems extends through the handle.

In one embodiment a handle is connectable with the edge of the applicator, and wherein preferably the handle is arranged as a tube and the agent channel can be conducted through the handle.

According to another aspect, the invention provides a device for a medical treatment of a sclera, the device comprising at least one applicator connected to a shaft, wherein:

each applicator is configured to be placed into the Tenon's space;

each applicator has a first surface and an opposite second surface, wherein the first surface of the applicator is superficially contactable to the surface of an area of the sclera so as to superficially cover said area; and each applicator and shaft comprises an agent channel extending from a proximal end of the shaft to a single distal opening at the first surface of the applicator, the proximal end of the agent channel being connectable to an agent supply;

an optical surface area connected to an optical guiding element extending from a proximal end of the shaft to the distal optical surface area at the first surface of the applicator, the optical guiding element being configured for guiding electromagnetic waves towards the optical surface element, and a bipolar electrode connected to an electrical conductor element extending from a proximal end of the shaft to the distal electrode at the first surface of the applicator.

In all embodiments the device may further comprise one or more sensor(s) or measurement system(s), such as a temperature sensor (in particular for embodiments where light and electrical coagulation is used) and/or a camera system (for example for endoscopic, minimal-invasive movement of the applicator(s)), and/or biomechanical sensor (for example for detecting whether or not the applicator contacts the sclera), preferably a pressure sensor, and/or a pH meter.

In all of the described embodiments, the device may comprise projections or a rim at the periphery of the applicator.

According to another aspect, the invention provides a method of treating the sclera in a subject comprising the steps of (i) placing of the applicator of the device of any of the embodiments into the Tenon's space in the eye of the subject so that the first surface of the applicator is superficially in contact with a surface of an area of the sclera, (ii) applying an agent to the sclera of the subject.

According to another aspect, the invention provides a method of treating the sclera in a subject comprising the steps of (i) placing of the applicator of the device of any of the embodiments into the Tenon's space in the eye of the subject so that the first surface of the applicator is superficially in contact with a surface of an area of the sclera, (ii) applying electromagnetic radiation to the sclera of the subject.

In one embodiment the method is for treating a pathological change or disease of the eye.

The device according to the invention:

can be adapted to anatomy and size of the eye enables extensive treatment of the scleral tissue (also of the posterior sclera)

enables temporally and locally controlled use of different systems (e.g. substance application and suction, radiation, visual control)

a homogeneous, extensive distribution of substances is possible due to surface modifications on the inside and outside of the system (impossible when using cannulas)

is able to combine different treatments (e.g., interconnection, coagulation and crosslinking).

The substance application and radiation system enables the extensive and/or local defined treatment of the outer sclera (the white tissue of the eye) for scleral collagen crosslinking and/or collagen coagulation. Through the application of special chemical substances and/or light of different wavelengths to the sclera it is possible to crosslink collagen molecules and thus change the biomechanical properties of the tissue. Thus, certain pathological changes and diseases of the eye (e.g. progressive myopia, scleritis, tissue-macerating inflammation, glaucoma, refractive errors, presbyopia) could be treated. These pathological changes minimize the biomechanical stability of the sclera and lead to an abnormal expansion of the eyeball and consequently to serious visual limitations or blindness. On the other hand it seems to be feasible that irradiation or another individual treatment alone might influence the biomechanical properties of scleral tissue to treat different eye diseases; e.g. complimentary to increasing the scleral stiffness for progressive myopia prevention it might be feasible to decrease the scleral tissue stiffness by blue light application alone to treat and/or avoid glaucoma development.

Furthermore, the substance application and radiation system (SAIS-Spot) according to the invention enables the extensive treatment of the outer sclera (the white tissue of the eye) for scleral crosslinking for the treatment of progressive myopia, pathological changes of the sclera or other biomechanical maceration symptoms that can be brought about by different causes (e.g. inflammation, local infections, scleritis). The therapeutic approach to these special diseases of the eye is new and requires—due to the complex anatomy of the eye—a surgical application system with adapted shapes and certain technical features.

On the other hand it seems to be feasible that irradiation or another individual treatment alone might influence the biomechanical properties of scleral tissue to treat different eye diseases; e.g. complimentary to increasing the scleral stiffness for progressive myopia prevention it might be feasible to decrease the scleral tissue stiffness by blue light application alone to treat and/or avoid glaucoma development.

BRIEF DESCRIPTION OF THE DRAWINGS

The invention will now be described in detail with regard to the following drawings:

FIGS. 2A-D show a device according to a first preferred embodiment of the invention;

FIGS. 3A-F show a device according to a second preferred embodiment of the invention;

FIGS. 4A-E show a device according to a third preferred embodiment of the invention;

FIGS. 5A-D show a device according to a fourth preferred embodiment of the invention;

FIGS. 8A-D show a device according to a ninth preferred embodiment of the invention;

FIGS. 9A-C show further examples of the device according the invention;

FIG. 10 shows another example of a device according to the invention;

FIGS. 14A-B shows light microscopy images of histological semi-thin sections (0.5 μm thickness, toluidin blue staining) to compare the dimensions and structure of scleral tissue from various species.

DETAILED DESCRIPTION OF EMBODIMENTS

Figure 1:
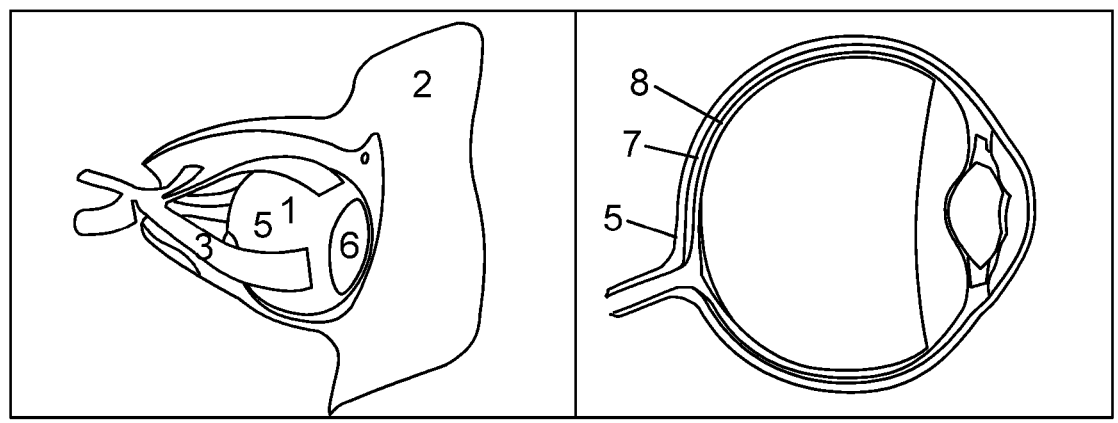
FIG. 1 shows a detailed representation of the eye's anatomy and its adnexa.

Protein (e.g. collagen) crosslinking is a method established in biotechnology. The crosslinking of proteins can be effected by chemical crosslinkers/agents or through photosensitive substances with subsequent radiation (e.g. riboflavin application and UV-A-light or blue light radiation). A further mechanism is the protein coagulation, for example due to the application of heat.

Collagen crosslinking is thus supposed to induce a connection of the molecules which change the biomechanical properties (stiffening). Collagen crosslinking through riboflavin application and UV-A-light radiation has been used for some years in ophthalmology for the treatment of patients with maceration diseases of the cornea (translucent part of the adventitia in the front part of the eye) (Wollensak et al., American Journal of Ophthalmology 2003, 135:620-627). Substance and light application are much easier in the front part of the eye since this part can be reached directly without surgery. However, the problems of the inhomogeneous radiation and substance distribution have not been completely eliminated here either.

Collagen crosslinking of the sclera (scleral crosslinking) for the treatment of progressive myopia and other maceration diseases is new and has so far only been tested in animal experiments (Iseli et al., Journal of Refractive Surgery 2008, 24:752-755; Wollensak et al., Acta Ophthalmologica Scandinavica 2005, 83: 477-482). All technical means in the animal experiments have various disadvantages and are not suitable for the use with patients.

Additionally, proteins and collagen can be crosslinked by an application of solely crosslinking chemical substances without a subsequent radiation (see "Chemical crosslinking and the stabilization of proteins and enzymes" by Wong S S, Wong L J. Enzyme Microb Technol. 1992 November; 14(11):866-74).

With the device according to the invention it is possible for the first time to extensively supply the rear and equatorial parts of the sclera locally defined and punctual with agents from the outside. Simultaneously, other systems can be used. Superfluous agents are removed. Additional modifications of the surfaces allow a better distribution of agents, and a better removal of the agents in the areas not to be treated, respectively. The device according to the invention is the prerequisite for a time saving (short surgery times) application of a new therapeutic approach with patients and in animal experiments. The device according to the invention is ergonomically adapted to the anatomy of the human eye. Its materials are sterilizable and reusable or may be produced as a disposal device.

The present invention allows for the locally and temporally controlled release and back flow of agents (e.g. substances, medicines) and allows the combination with other physical applications (electromagnetic radiation) on defined areas of the sclera. It also allows the combination of crosslinking with collagen coagulation. The present invention additionally allows for the locally and temporally controlled irradiation and application of defined power levels of electromagnetic radiation (i.e. energy amount per time and area).

The outer, surrounding collagenous layer of the eye is the sclera (white part) and the cornea (translucent part; FIG. 1). In some diseases, this tissue part of the eye is weakened. This can be the case with respect to biomechanical stability, enzymatic resistance to digestion or in respect to its swelling behaviour. This debilitation of the eye (cornea and sclera) can be positively influenced through crosslinking or collagen coagulation. For this, an agent (fluid) has to be introduced into the respective tissue layer of the eye, either with or without additional additives e.g. electromagnetic radiation, a second agent), to start chemical or physical reactions. These reactions lead to changed biomechanical properties and to an improvement of the treated layers of the eye with respect to the above-mentioned weaknesses. This treatment is called "crosslinking".

FIG. 1 shows a detailed representation of the eye's anatomy and its adnexa. The left image shows the eye 1 in the orbital cavity (bone 2) with its muscular connections 3. The eye 1 lies in the orbital cavity in a periscleral lymph space, i.e., the Tenon's space which is usually closed to the front between the corneal limbus 4 and the eyelid (not shown here). The sclera 5 is the white part of the outer eye, the cornea 6 the translucent part of the eye 1. Both tissues are made from collagenous tissue. The right image shows a detailed labeling of the anatomical layering of the inner tissues of the eye 1. In the right image, the tissue structures of sclera 5/choroid 7/retina 8 are highlighted.

In the scleral part, the eye ball is surrounded by a very thin submucosa, the episclera (not shown separately), which is connected to the sclera 5.

The device according to the invention enables the extensive treatment of the outer sclera for scleral collagen crosslinking and or collagen coagulation. The device (SAIS-Spot) according to one embodiment preferably is a flat, large-scale and spoon-like bent ophthalmological surgical instrument with variable areal shape for the dosed release of substances/agents to the sclera or parts of it.

The exact areal shapes and dimensions of the SAIS-Spot result from the precise anatomical characteristics of the eye or even of the individual patient or the individual patients' clinical and therapeutic needs. Furthermore, the exact areal shapes and dimensions of the SAIS-Spot result from the determined minimal areas that need to be treated for growth inhibition. Therefore, the SAIS-Spot can have varied shapes, preferably areal shapes, that are of simple or complex form or that may even be calotte-shaped and cover the whole scleral part of the eye. A small spot is also encompassed by the invention.

FIG. 2A shows a first exemplary embodiment of the device of the invention. The device shown in FIG. 2A has a single applicator 21 with a shaft 22. Upon use of the device, the applicator 21 is placed between two neighbouring muscular connections 3.

FIG. 2B shows a modified first exemplary embodiment of the device of the invention. The device shown in FIG. 2B has two applicators 21 each with a shaft 22. The two shafts 22 are merged into proximal shaft 23. Upon use of the device, each applicator 21 is placed between two neighbouring muscular connections 3.

The cross sectional view of FIG. 2C shows a cylindrical applicator 21a with a central optical guiding element 25 surrounded by a sheath 26. The optical guiding element 25 is suitable for the application of light, e.g. UV- or blue light. This is indicated by the black arrow. Additionally, agent channels 27, 28 are provided. One agent channel, i.e. agent channel 27, is used in this example for the application of an agent such as riboflavin (see also grey arrow pointing towards the distal end of the applicator), whereas the other channel 28 is used for sucking away superfluous agent (see grey arrow in proximal direction).

The cross sectional view of FIG. 2D shows a flat applicator 21b having an optical guiding element 25 surrounded by a sheath 26. The optical guiding element 25 is suitable for the application of light, e.g. UV- or blue light. This is indicated by the black arrow. Additionally, agent channels 27, 28 are provided side-by-side with the optical guiding channel 25. One agent channel 27 is used in this example for the application of an agent such as riboflavin (see grey arrow in distal direction), whereas the other channel 28 is used for sucking away superfluous agent (see grey arrow in proximal direction).

FIGS. 3A-F shows a second exemplary embodiment of the device of the invention. The device shown has two small curved or plane applicators 10 each with a shaft 22. The two shafts 22 are merged into proximal shaft 23. Upon use of the device, each applicator 10 is placed between two neighbouring muscular connections 3. FIGS. 3B and 3C also shows two exemplary schematic cross-sectional views of the applicator 10 (showing, FIG. 3B, the slightly curved shape, and, FIG. 3C, a flat shape) and three alternative surface configurations of the applicator 10. In FIG. 3D, the applicator comprises two spots 25 that allow a punctual application of light, heat, and/or two spots 27, 28 for the application of an agent onto the sclera. Alternatively, as shown in FIG. 3E, four spots 25 are provided arranged in at the corners of a virtual square. Two spots 27, 28 for the application of an agent onto the sclera are also shown. As a further alternative as shown in FIG. 3F, the "spot" 25 covers a substantial area of the applicator 10. The basic outer shape of the applicator in these examples is that of a square.

FIG. 4A shows a third exemplary embodiment of the device of the invention. The device shown has two curved applicators 20 each with a shaft 2. The two shafts 2 are merged into proximal shaft 23. Upon use of the device, each applicator 20 is placed between two neighbouring muscular connections 3. FIG. 4B shows a schematic cross-sectional view of the applicator 20 (showing the slightly curved shape). Three alternative configurations of the applicator 20 are shown in FIGS. 4C-E. In FIG. 4C, the applicator 20 comprises four spots 25 arranged along a virtual line that allow a punctual application of light, heat, and/or an agent onto the sclera. Alternatively, as shown in FIG. 4D, a pattern of eight spots 25 is provided arranged along two parallel virtual lines. As a further alternative in FIG. 4E, the "spot" 25 covers a substantial area of the applicator 20. The basic outer shape of the applicator 20 in these examples is that of an elongate oval or rectangle with curved corners.

FIG. 5A shows a fourth exemplary embodiment of the device of the invention. The device shown has two curved applicators 30 each with a shaft 22. The two shafts 22 are merged into proximal shaft 23. Upon use of the device, each applicator 30 is placed between two neighbouring muscular connections 3. FIG. 5B also shows a schematic cross-sectional view of the applicator 30 (showing the slightly curved shape). FIGS. 5C and 5D show two alternative configurations of the applicator 30. In FIG. 5C, the applicator 30 comprises four spots 25 arranged along a virtual line that allow a punctual application of light, heat, and/or an agent onto the sclera. As a further alternative, the "spot" 25 in FIG. 5D covers a substantial area of the applicator 30 (in the shown alternative in the form of a rectangle). The basic outer shape of the applicator 30 in these examples is that of a rectangle. Here, the applicator 30 is also elongate and narrow in shape.

FIG. 6 shows a fifth exemplary embodiment of the device of the invention. In this embodiment, the applicator is adapted for larger treatment areas. The device shown has two curved applicators 40 each with a shaft 22. The two shafts 22 are merged into proximal shaft 23. Upon use of the device, each applicator 40 is placed between two neighbouring muscular connections 3. FIG. 6B shows a schematic cross-sectional view of the applicator 40 (showing the slightly curved shape). FIGS. 6C to 6E show three alternative configurations of the applicator 40. In FIG. 6C, the applicator 40 comprises three spots 25 that allow a punctual application of light, heat, and/or an agent onto the sclera. Alternatively, as shown in FIG. 6D, six spots 25 are provided arranged along two parallel virtual lines. As a further alternative in FIG. 6F, the "spot" 25 covers a substantial area of the applicator 40. The basic outer shape of the applicator in these examples is that of a square.

Figure 7A:
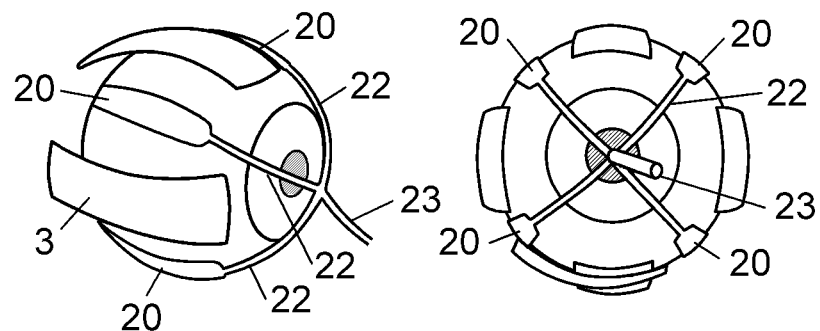
FIG. 7A shows a device according to a sixth preferred embodiment of the invention.

FIG. 7A shows a sixth exemplary embodiment of the device according to the invention. This embodiment is similar to the embodiment of FIG. 4 but has four applicators 20. Upon use of the device, each applicator 20 is placed between two neighbouring muscular connections 3. This allows the treatment of all areas at the same time. In this embodiment, however, it is possible to control each applicator 20 individually and separately. The front view (right in FIG. 7A) shows the arrangement of the four applicators 20 between the muscular connections 3.

Figure 7B:
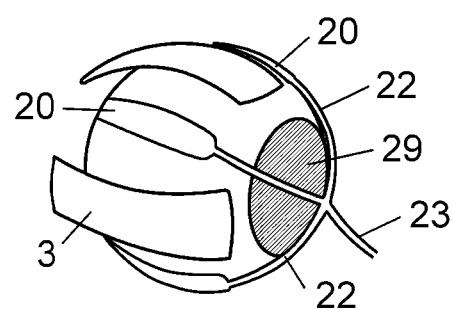
FIG. 7B shows a device according to a seventh preferred embodiment of the invention.

A further modified embodiment is shown in FIG. 7B. Here, the device additionally comprises a cornea shield 29. The cornea shield serves at least two purposes: it protects the eye, and it fixes the applicators 20.

Figure 7C:
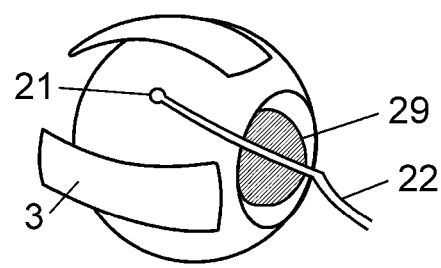
FIG. 7CA shows a device according to a eighth preferred embodiment of the invention.

In the alternative shown in FIG. 7C, just a single applicator 21 is present, like the one shown in FIG. 2A. Also in this embodiment, a cornea shield 29 is present. Here, the shield may also serve to assist in proper positioning of the applicator 21.

In general, the cornea shield may be a partial cornea shield only.

FIG. 8 shows another example. This example is similar to the embodiment shown in FIG. 2. It shows at the center the optical channel output 83 for the application of light. In addition, optional camera(s) 84 are provided as well as two temperature measurement sensors 85. Furthermore, two agent channels 81 are provided for the application and suction of riboflavin. Furthermore, two spots 82 are provided for protein coagulation. As shown in FIG. 8B, the optical fiber 82 used for coagulation is at least partially coloured adapted to generate heat. Due to the just partial coating, light that is not absorbed by the coating but passes can additionally be used for crosslinking. Although some of the channels or spots are shown are shown as a pair, the invention also encompasses that only a single one of each channel or spot is present. Alternatively any combination of one or two channels and spots is encompassed.

FIG. 8C shows a schematic side view of the applicator 21, whereas FIG. 8D shows a bottom view of the applicator 21 with its shaft 22.

FIG. 9 shows different structures of the first surface of the applicator according to the invention. According to FIG. 9A, the first surface 91 is flat. The bottom view of FIG. 9A, i.e. the view onto the first surface 91 of the applicator 90a, shows four elements 80 according to FIG. 8 arranged across first surface 91.

In the alternative of FIG. 9B, the applicator 90b is flat with projections The bottom view of FIG. 9B, i.e. the view onto the first surface 91 of the applicator 90b, shows five elements 80 according to FIG. 8 arranged across first surface 91.

In the third alternative of FIG. 9C, the applicator 90c is flat with seven projecting elements 80 according to FIG. 8 and rim 92.

FIG. 10 shows another example comprising a riboflavin agent supply 102, light and/or heat emitting elements 80. In this example, a diffuser 101 is provided for aerial crosslinking. The elements for heat application (protein coagulation) might end in a sharp tip to improve the positioning of the applicator and/or to increase the scar inducing procedure (deeper penetration into the tissue).

Figure 6E:
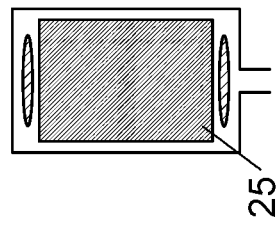
FIGS. 6A-E shows a device according to a fifth preferred embodiment of the invention.
Figure 6D:
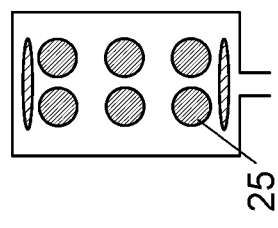
Figure 6C:
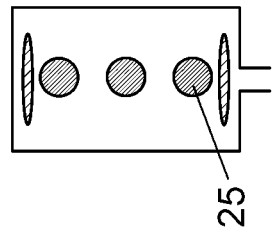
Figure 6B:
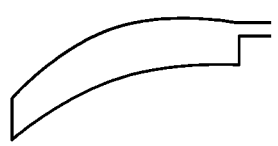
Figure 6A:
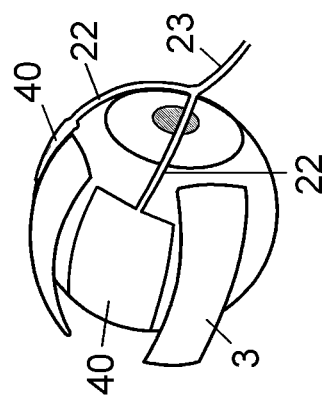

FIG. 17 shows different treatment patterns that can be obtained with the devices/applicators according to the present invention. According to FIGS. 17A to 17C, the treatment is by "serial" application of individual spots in a desired pattern. An applicator as shown in FIG. 2A or 7C can be used to apply such pattern. In FIG. 17D to 17F, at least two spots are applied at a time, i.e. with a multi-spot applicator as shown in FIG. 3D, 3E, 4C, 4D, or 5C, for example. A pattern obtained with an applicator according to FIG. 6C or 6D is shown in FIG. 17F. It shows a pair wise arrangement of the spots for thermal coagulation. In the area between the spots (shown in lighter grey), regular aerial crosslinking is applied.

The optical fibers (also called optical waveguide or glass fiber) can be selected in different realizations and have to be able to conduct electromagnetic radiation of different wavelengths (UV light to infra red light, from approximately 300 nm-1100 nm). Some structural realizations of the SAIS-Spot can then be optimized for specific wavelengths of the electromagnetic radiation and specific light energy levels. Thus, specific optical fiber materials (e.g. extra UV light conductive) and specific optical fiber diameters (e.g. larger cable diameters for high energy levels) can be used for the SAIS-Spot. The optical fibers of the device should be able to project radiation energy levels of 1-300 mW/cm$^2$ onto the inner surface of the device. The light for the optical fibers in the SAIS-Spot is provided by an externally controllable and adjustable radiation source (e.g. different LEDs in one LED unit, different lasers, or different lamp types). The external radiation source is controllable (i) in the radiated wavelength, (ii) in the radiation energy level and (iii) in the application time (length and sequence of the radiation impulses). Thus, control of the luminous power (radiation energy level per time unit) of the device is guaranteed by the external radiation source which controls the optical fibers. In addition, it is possible with this external light source to separately control specific groups of optical fibers and to thus individually illuminate certain areas of the SAIS-Spot inner surface. It is thus possible to simultaneously provide different areas of the inside of the SAIS-Spot with different wavelengths and different radiation energy levels.

The optical fibers and/or their ends can be arranged in different ways on the inside of the SAIS-Spot (within the diffuser).

Within the device, the feeding of substances and radiation is completely separate (optically opaque materials for the channels, possibly in addition mirrored optical fibers or normal optical fibers with total internal reflection, respectively) so that light-sensitive substances are not influenced and changed within the SAIS-Spot through radiation. Substance feeding and the radiation unit are also controllable temporally separately through the external coupling devices.

After opening the tissue connection between the orbital cavity and the bulb, the device of the invention is introduced into the Tenon's space. The device is placed on the equatorial and lateral part of the sclera, past the muscles. There, it is possible to apply substances or radiation during surgery without having to remove the device from the site to be treated (Advantages: (i) saves time during surgery, (ii) even or especially chosen distribution of substance application and radiation, (iii) less risk of damaging the surrounding tissue due to repeated insertion and removal of surgical instruments).

The device according to the invention can also be equipped with a temperature probe within the diffuser (inner part of the SAIS-Spot). The feeding or the connection to the recording unit ensues in the same manner as the integration of the optical fibers in the diffuser. Additional equipment may be used to determine whether the applicator contacts the sclera.

The SAIS-Spot can also be combined with a video surveillance system, wherein an endoscopic visualizing system is attached to/integrated into the SAIS-Spot.

In this context, the agent is preferably a chemical cross linker or a photosensitive substance. The photosensitive substance is for example riboflavin. Riboflavin can for example be applied followed by the application of light radiation or a protein coagulator.

The light radiation in the context of the devices and methods of the present invention is preferably UV-A light radiation (about 315 to about 380 nm, e.g. about 370 nm) or "blue light" radiation ("blue light" means that it has preferably a wavelength of from about 420 to about 480 nm, preferably about 425 to about 475 nm, more preferably about 450 to about 465 nm; preferred wavelengths are about 450 nm and about 465 nm), particularly when riboflavin is used as the photosensitive substance. When the light radiation is UV-A light radiation, the light intensity is for example in the range of 1 to 200 mW/cm$^2$, preferably 2 to 4 mW/cm$^2$, at the surface of the sclera. When the light radiation is "blue light" radiation, the light intensity may generally be higher than with UV-A radiation, for example it can be in the range of 1 to 350 mW/cm$^2$, preferably it is between 10 and 200 mW/cm$^2$, more preferably between 20 and 100 mW/cm$^2$, and even more preferably between 25 and 100 mW/cm$^2$ at the surface of the sclera. In general, when pulsed light is used higher light intensities may be used as compared to the application of continuous radiation. In certain embodiments, band pass filters may be used to create certain light profiles, e.g. 320 to 400 nm or 420 to 480 nm or 425 to 475 nm or 450 to 465 nm.

The pathological change or disease of the eye may in the context of the present invention for example be selected from the diseases and conditions discussed herein above and in particular selected from progressive myopia, scleritis, and pathological changes of the sclera such as tissue-macerating inflammation.

The invention also pertains to the device as described herein above for use in the treatment of a pathological change or disease of the eye.

Exemplary Procedure for Scleral Crosslinking Using the SAIS-Spot Device

Aim of the surgical procedure is to crosslink the collagen molecules in the scleral tissue of patient eyes by application of riboflavin as a photosensitizer and a combined irradiation with blue light. Riboflavin and/or the light irradiation (preferably both) are applied using the SAIS-Spot device. Other photosensitizers and electromagnetic irradiation of another wavelength may also be used.

In the present procedure for the sclera crosslinking (SXL) of human eyes, 0.01-20%, preferably 0.5% riboflavin in isotonic NaCl solution is applied to the surface of the entire sclera (or only areas which should be treated) for 1 seconds-40 minutes, preferably 60 seconds to 30 minutes before the irradiation starts. The riboflavin solution might be pre-warmed (e.g. up to about 35° C.) before application, e.g. using a heated reservoir or a heating system in the device. The riboflavin solution may also be modified e.g. in terms of its viscosity or its tissue penetration behavior by adding dextran or another supplementary substance. The application of riboflavin may be repeated consecutively/alternately during the irradiation procedure or alternatively may only be applied in the beginning.

The irradiation power of blue light may be between about 1 to 2000 mW/cm$^2$, preferably it is between 10 and 200 mW/cm$^2$, more preferably between 20 and 1000 mW/cm$^2$, and even more preferably between 25 and 100 mW/cm$^2$ blue light power on the human scleral tissue. It is also possible to apply other electromagnetic wavelengths e.g. UV-light such as UV-A, or a combination of two or more different wavelengths alternately or simultaneously during a treatment. Furthermore, it is possible to apply light of a certain bandwidth of electromagnetic wavelengths (e.g. blue light with a bandwidth from 420 to 480 nm; see above)

The scleral tissue can for example be irradiated 1 second to 40 minutes, preferably approximately 20 min with an optimal blue light power (as discussed above) during the SXL operation. The irradiation time intervals may e.g. be 1-30 seconds, preferably 10-30 seconds with an interruption of e.g. 10 seconds to avoid any kind of locally spreading thermic stress for the scleral tissue or can be continuous or pulsated in any way. Fresh riboflavin solution may be applied alternately e.g. every 5 minutes during the blue light irradiation to refresh the used riboflavin and additionally, to cool the irradiated scleral tissue. It may also be applied continuously. Other irradiation intervals and frequencies and prolonged or shortened irradiations procedures are feasible in dependence of the light power. This is a crucial advantage of the SAIS-Spot device in comparison to other light sources: the position of the SAIS-Spot need not be changed or retracted and repositioned during the entire irradiation procedure because riboflavin application is possible simultaneously. After SXL treatment the substance application and aspiration channel part of the SAIS-Spot device can be used to remove excessive riboflavin and to flush the orbita with sterile isotonic NaCl solution.

Additionally, this substance application and aspiration channel part of the SAIS-Spot device can be used to flush the Tenon's spaces with a variety of flushing solutions. These solutions might contain pharmacologically active substances or molecules to support or stabilize the SXL treatment outcomes. E.g. fibroblasts may be activated as a response to the crosslinking treatment. The fibroblasts may e.g. change their morphology, intracellular ultrastructure and/or metabolism, and may increase in numbers. Changes of the collagen bundle and fibril structure (increased number of small size collagen fibrils) may be observed as a sign of remodelling of the collagen bundle structure. These remodelling processes might be supported by proliferation activity or migration of fibroblasts and changes of the gen and protein expression profile. Thus, it might be that matrix-metallo-proteinase (MMP) will be produced for the remodelling process of collagen and extracelluar matrix components. TIMPs are the regulatory proteins for the inhibition of MMP activities. Therefore, it is feasible that pharmacologically active substances are applied after the SXL treatment to modulate the activity of MMPs and/or TIMPs. Pharmacologically active substances applied via the SAIS-Spot device can also modulate the activity of collagen producing gens or the naturally occurring collagen crosslinking enzymes (e.g. lysyloxidase) or those substances can regulate the proliferation and migration of fibroblasts and other blood derived cells.

Exemplary Surgical Procedure of SXL in Human Patients

To perform surgery for scleral crosslinking (SXL) anaesthesia is mandatory. It might be any kind of local anaesthesia by means of retrobulbar or parabulbar injection of anaesthetics or a general anaesthesia. Local anaesthesia with a topical application of eye drops or the total omission of anaesthesia is not recommended and is very unlikely. Preferably, a full anaesthesia is performed in combination with the application of a muscle relaxant. It might be necessary to inject additionally a retrobulbar block and/or to drop local anaesthetics onto the eye. The entire surgical procedure (anaesthesia, pre- and post-operative procedures and SXL) may take between 10 minutes and 3 hours.

The SXL treatment is performed on a horizontally stabilized patient. Disinfection may e.g. be performed by applying Povidone-Iodine or any other disinfection solution with high care to the ciliary body and the conjunctiva. A common surgical cloth is used to cover the patient while the eye keeps accessible for operation.

It is possible to use indirect ophthalmoscopy, a yellow band pass filter and/or an operation microscope while performing surgery.

After disinfection a lid speculum will preferably be inserted under the lids to keep the lids wide open. An operation without using a lid speculum is feasible but not preferred. During the following steps artificial tears will be dropped onto the exposed parts of the eye (cornea, sclera and/or conjunctiva). After keeping the lids wide open by the speculum, the conjunctiva will be incised by a scalpel or a small scissors and the conjuctiva will be separated from the limbus. In cases of bleeding from small blood vessels the bleeding will be stopped (for instance by a heat treatment—cauterization) and the blood will be removed. A partial or total incision of the conjunctiva around the entire eye (i.e. superior and inferior part of the lid/eye) and a complete separation of the conjunctiva from the limbus is recommended. It is also possible to reduce the dimension of the incision or in some cases it might only be necessary to open one part of the conjunctiva (superior or inferior). This depends on the shape and structure of the SAIS-Spot device and the sclera area to be treated. The complete incision of the conjunctiva enables the access to the Tenon's space in the orbita. Now, the four straight eye muscles are looped by an insertion of a thread behind the muscles and that enables the manipulation and orientation of the eye. In some cases it might not be necessary to manipulate the eye muscles or the entire eye. This depends on the shape, structure and size of the SAIS-Spot device which will be inserted. The SAIS-Spot can consist of only one relatively small spoon-like applicator with a simple shape or of two, three, or four applicator parts with complex shapes adapted to the anatomy of the eye or the requirements of the patient and/or the pathology which has to be treated. The shape may also be adapted to the minimal required area to be treated. The various parts of the applicator can be introduced simultaneously into the Tenon's space around the eye bulbus or the treatment can be carried out consecutively. This depends on the scleral area which has to be treated. Simultaneous insertion of several parts of the SAIS-Spot applicator reduces the operation time. Specifically adapted shapes of the SAIS-Spot device avoid the undesirable crosslinking of muscles, larger blood vessels, surrounding tissue and the optic nerve. It is possible to customize the shape of the applicator for each patient to be treated.

After the insertion of the SAIS-Spot device and its correct placement onto the bulbus the substance application starts and the sclera will be incubated with riboflavin e.g. for at least 1 second (as discussed above: various incubation periods and different concentrations and mixtures of riboflavin and other therapeutically substances are possible). It is possible to reduce the incubation time by adding other therapeutically substances.

After this pre-incubation the light irradiation starts (see above). During the irradiation period the riboflavin substance is applied alternately in a certain regime to refresh the used/bleached riboflavin. Used or excessive riboflavin can be aspirated by the SAIS-Spot aspiration channels.

Additionally, this substance application and aspiration part of the SAIS-Spot device can be used to flush the Tenon's spaces with various flushing solutions (see above). After SXL treatment and an optional flushing period with various substances the SAIS-Spot applicator/-s can be retracted from the orbita. Then the threads around the eye muscles should be removed and the conjunctiva has to be surgically closed by suturation. The treated patient eye may be medicated with topic antibiotics, antimycotics and/or steroid ointments or eye drops. In some cases this medical treatment is not mandatory. The eye may be taped and shielded by eye patches, eye ointment dressing and/or tamponade. After operation the patient should be kept under supervision of the anaesthesiologist and should be monitored by an ophthalmologist.

Other aspects, features, and advantages will be apparent from the description, including the figures and the claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

EXAMPLES

Example 1: Surgical Procedure in Rabbit Experiments

To perform the riboflavin/blue light collagen crosslinking the animals were anesthetized by an intramuscular injection of ketamine hydrochlorid (50 mg/kg body weight weight; Ketamin 5%, Ratiopharm, Ulm, Germany) and xylazinhydrochlorid (10 mg/kg body weight; Rompun; Bayer Vital GmbH, Leverkusen, Germany). For maintenance of the anaesthesia Ketamine hydrochloride (25 mg/kg body weight) and xylazinhydrochlorid (5 mg/kg body weight) were injected intramuscular. Only the right eye underwent treatment whereas the contralateral untreated eye served as individual control. For avoiding corneal damage while surgery the left eye was treated with Floxal® eye ointment (Dr. Gerhard Mann GmbH, Berlin, Germany). Conjuncain was additionally used for local anaesthesia of the right eye. After temporal canthotomy the conjunctiva was incised at the limbus to open the Tenon's space. Then Tenon's space was bluntly dissected in the superior temporal quadrant. The superior rectus muscle and the temporal rectus muscle were displayed and fixed by means of 5/0 Prolene sutures (Ethicon, Norstedt, Germany) to allow better exposition of the sclera and easier manipulation of the eye position during scleral treatment. Then riboflavin-5'-phosphate (Vitamin B2, 0.5% in PBS without any Dextran admixture, Streuli Pharma, Uznach, Switzerland) was dropped every five minutes on the exposed sclera to assure the plain penetration of riboflavin into the scleral stroma. After 20 minutes of soaking the temporal sclera was irradiated 20 min with one of the different intensities (10, 25, 50, 100, 200, 400 and 650 mW/cm$^2$) of blue light (450±25 nm) using a commercial dental light source (Bluephase 16i, Ivoclar Vivadent GmbH, Ellwangen-Jagst, Germany), matching one absorption maximum of riboflavin (450 nm). Here an irradiation of the cornea and the retina had to be avoided because of the destructive properties of blue light for the corneal and retinal tissue. Riboflavin drops were applied every 5 min during the entire irradiation period to avoid excessive photo-bleaching of the fluorophore. The adjustment of the applied light intensity (10 mW/cm$^2$ up to 400 mW/cm$^2$) was realized by custom built polypropylene spacing tubes and measured with a power meter in combination with a visible light sensor (LaserMate Q, Coherent Inc., Santa Clara, Calif., USA). A light intensity of 650 mW/cm$^2$ was realised by the light source without an additional spacing tube. After irradiation, the sutures were removed and the connective tissue was attached to the sclera using absorbable surgical sutures. Finally the canthothomy was readapted with absorbable surgical sutures. Both eyes were treated with Floxal® eye ointment (Dr. Gerhard Mann GmbH, Berlin, Germany) into the conjunctival fornix and the cornea avoiding infection and drying. The animals were monitored till awakening and kept in the Medizinisch-Experimentelles Zentrum of the University of Leipzig for 3 weeks.

Example 2: Measurement of Riboflavin Penetration in Scleral Tissue

Figure 11:
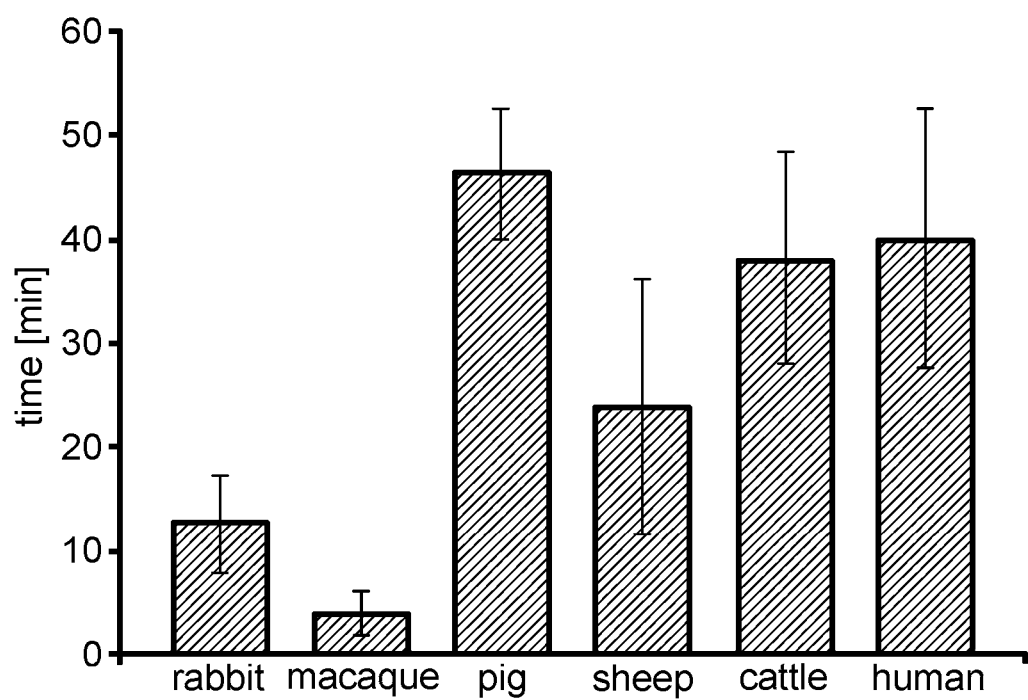
FIG. 11 shows the mean time period of the total tissue penetration of Riboflavin in scleral patches from various species.
Figure 12A:
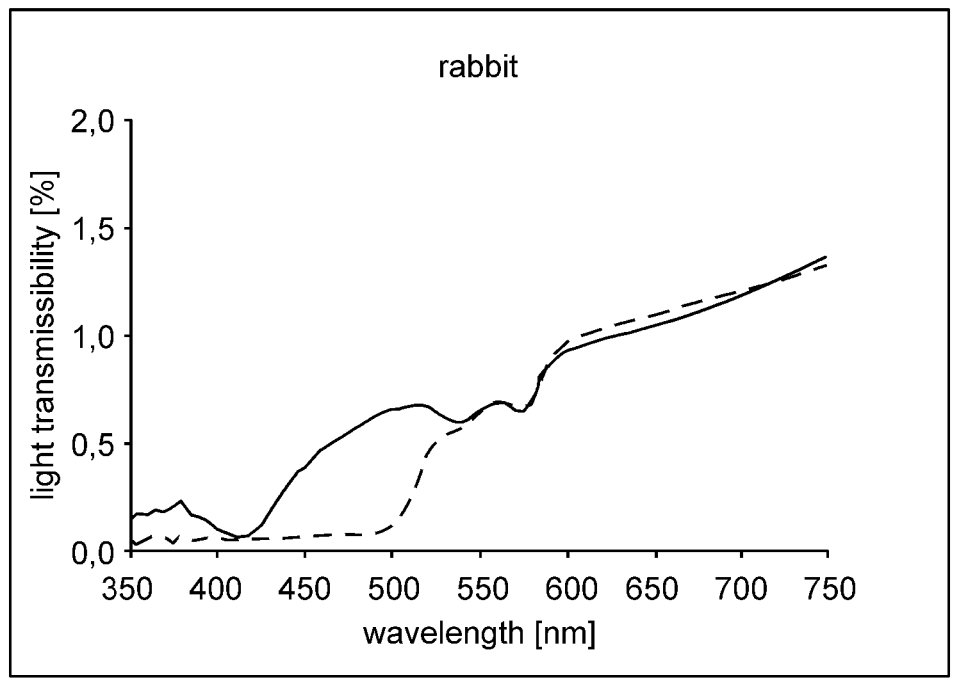
FIGS. 12a-f demonstrates the spectral light transmissibility characteristics of scleral tissue from various species with (dotted line) and without (continuous line) riboflavin application.
Figure 12B:
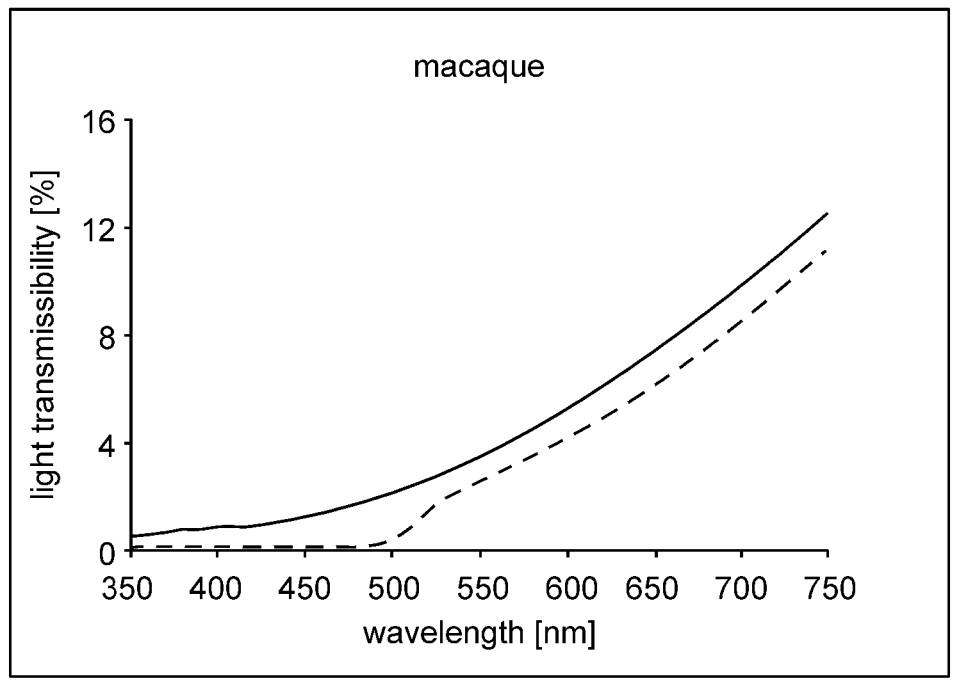
Figure 12C:
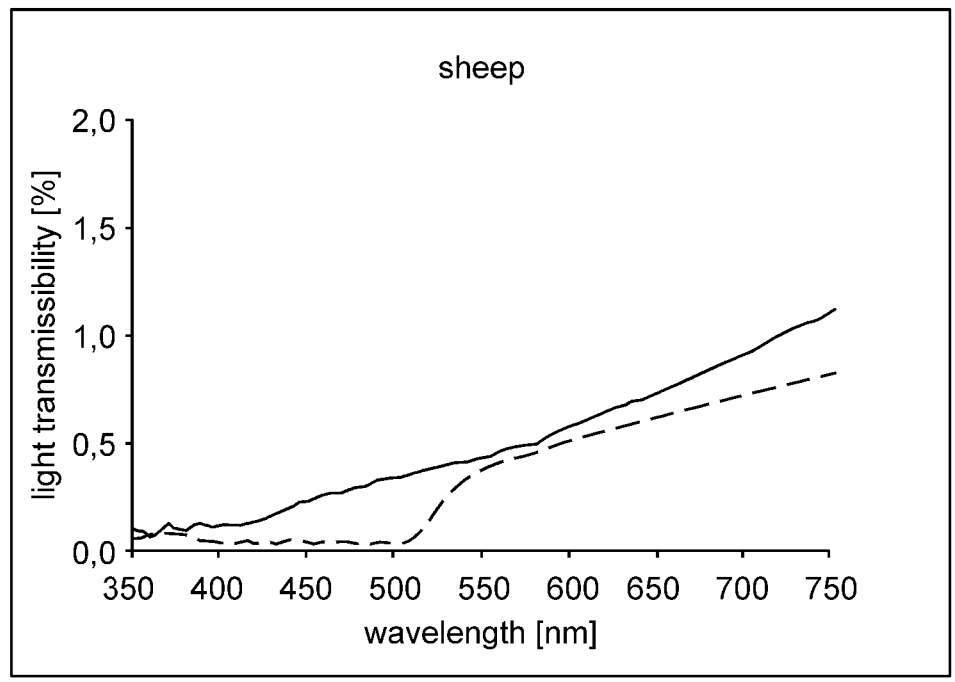
Figure 12D:
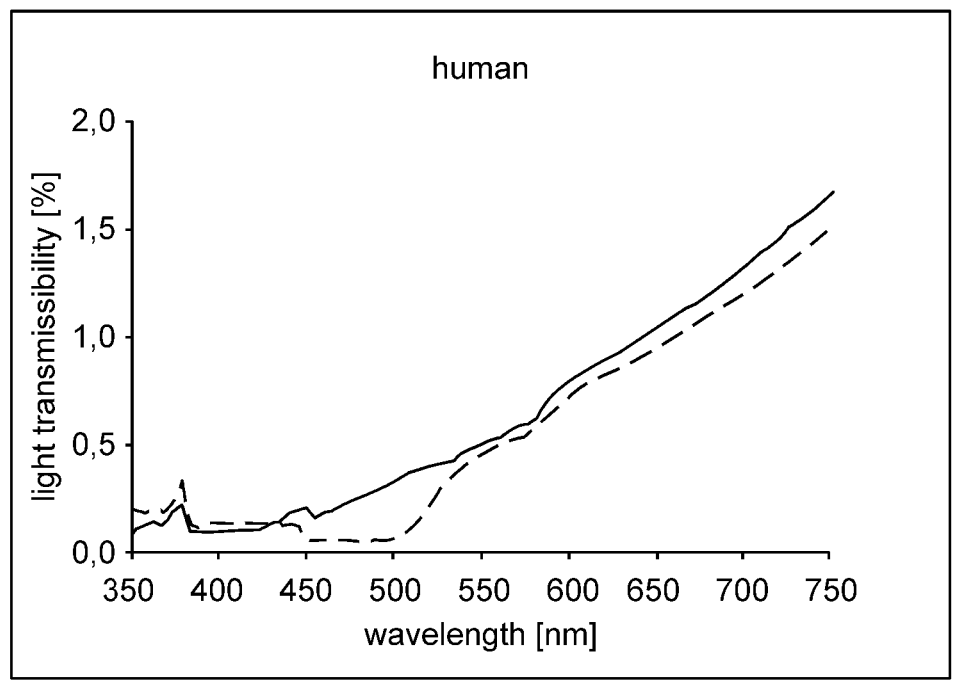
Figure 12E:
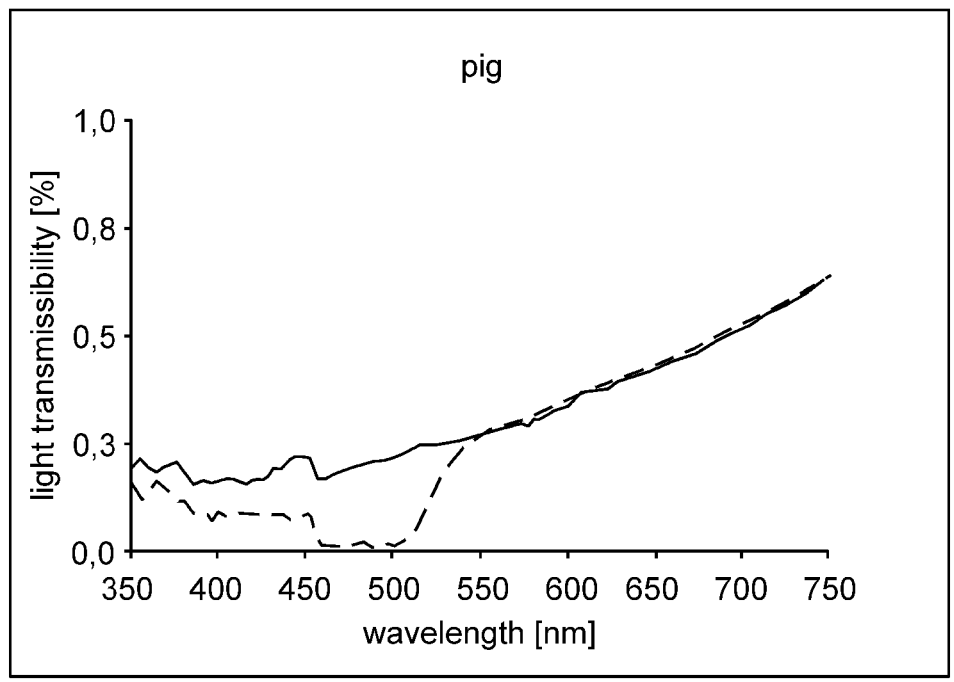
Figure 12F:
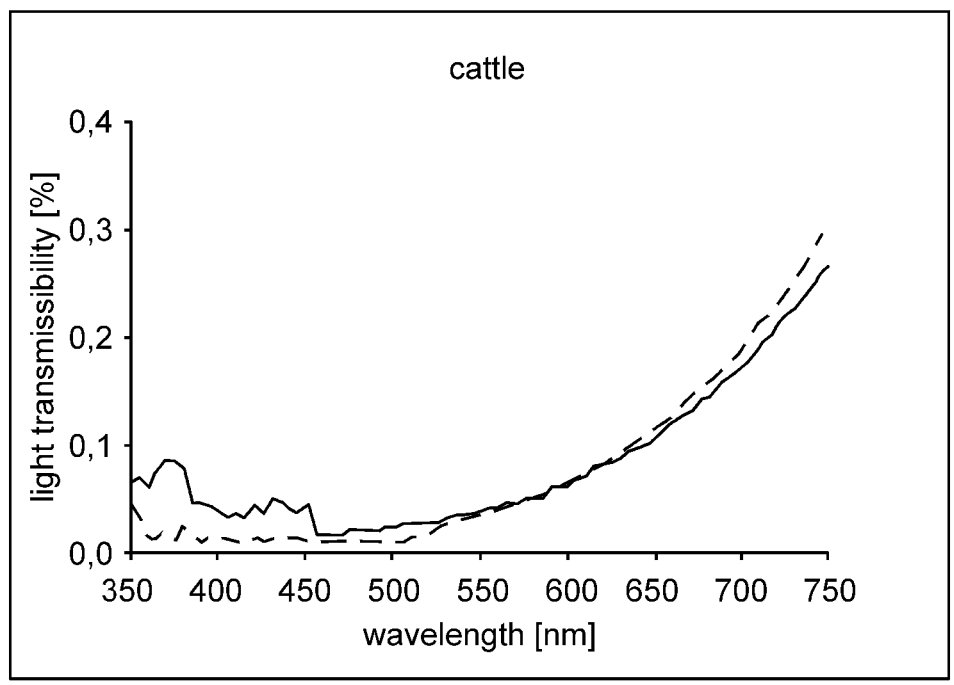

FIG. 11 displays the mean time period of the total tissue penetration of Riboflavin in scleral patches from various species. The penetration time was calculated by an application of riboflavin onto one side of a scleral tissue patch and the total appearance on the opposite side monitored as a maximum of fluorescence by a fluorescence microscope. Compared to 10-20 minutes in rabbit sclera, it takes approximately 30-40 minutes for riboflavin to penetrate the human sclera. Frozen/thawed scleral tissue was used for this examination; however, the results were similar with freshly isolated (i.e. non-frozen) tissue.

FIG. 12 demonstrates the spectral light transmissibility characteristics of scleral tissue from various species. Approximately only 0.5-1% of the light (up to 500 nm wavelength) penetrates the scleral tissue of all species. The application of riboflavin reduces the transmissibility further at wavelength up to 530 nm caused by the strong light absorption of Riboflavin at that wavelengths.

Figure 13:
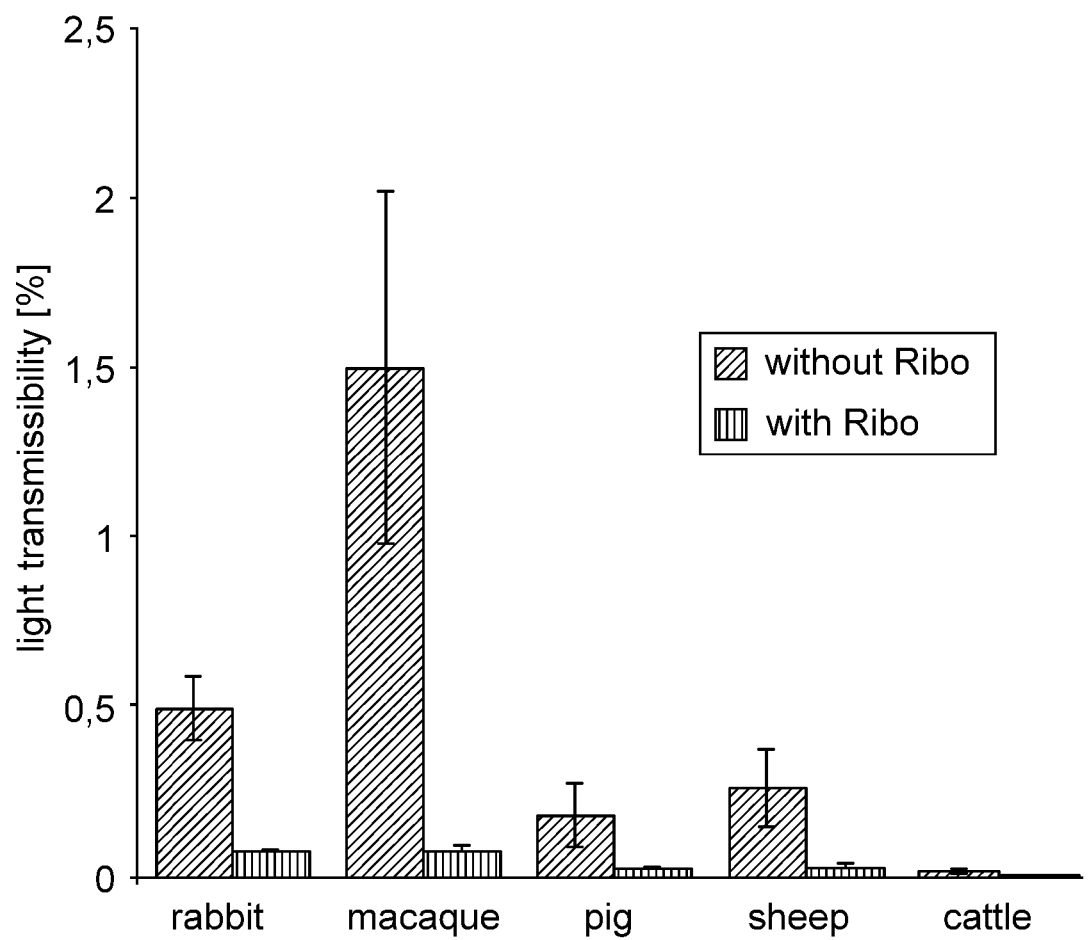
FIG. 13 shows the light transmissibility characteristics of freshly isolated scleral tissue from various species at a wavelength of 450 nm with and without riboflavin application.

FIG. 13 demonstrates the light transmissibility characteristics of freshly isolated scleral tissue from various species at a wavelength of 450 nm. Approximately only 0.5% of the light penetrates the scleral tissue of all species. The application of riboflavin ("Ribo") reduces the transmissibility further at 450 nm caused by the strong light absorption of riboflavin at that wavelength.

Example 3: Results of Sclera Crosslinking in Different Species

FIG. 14: Light microscopy of histological semi-thin sections (0.5 μm thickness, Toluidin blue staining) to compare the dimensions and structure of scleral tissue from various species. The scale bar in A (macaque) sclera is valid for all scleral sections in A and demonstrates the differences of thickness in the posterior part of the sclera. B shows histological sections at higher magnification to reveal structural differences. The histological examinations revealed large structural similarities between rabbit and human sclera and differences in comparison to other species. The scale bar in B (macaque) sclera is valid for all scleral sections in B.

Figure 15:
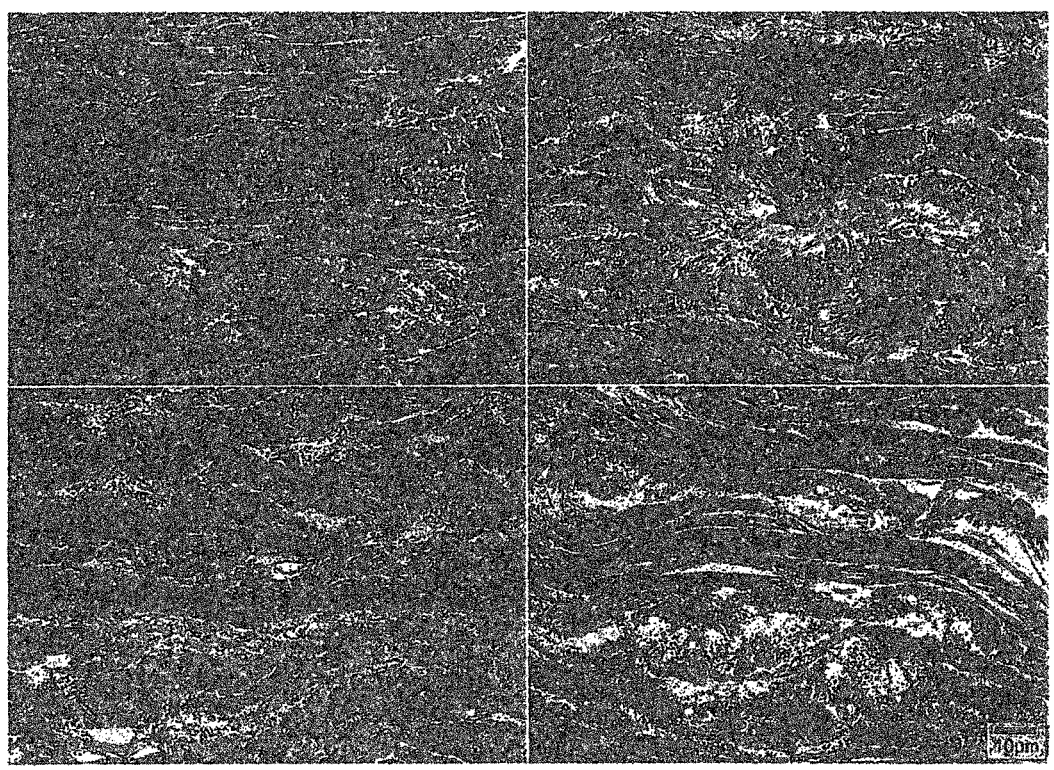
FIG. 15 shows microphotographs demonstrating the comparison of morphological properties of acute isolated (A; top left) and frozen/thawed (B-D) scleral tissue with (C; bottom left; and D; bottom right) and without (A and B) crosslinking treatment.

FIG. 15: Comparison of morphological properties of acute isolated (A) and frozen/thawed (B-D) scleral tissue with (C and D) and without (A and B) crosslinking treatment. Microphotographs display histological semithin sections of scleral tissue visualized by light microscopy (Toluidin blue staining). A: Acute isolated non-treated scleral tissue is characterized by a very compact collagen bundle arrangement and spindle-like ellipsoid cell bodies of fibroblasts (arrows) between the collagen bundles. B: Thawed (former frozen for storage) scleral tissue show a loosen bundle structure and contorted bundles (asterisks) in comparison to acute isolated scleral tissue. C: No dramatic changes of the overall structure of (thawed) scleral tissue were obvious after crosslinking treatment with riboflavin and 25 mW/cm$^2$ compared to the untreated thawed tissue in B. Cell bodies of fibroblasts appear swollen (arrow) and the bundle structure is contorted (asterisks). D: After a crosslinking treatment with riboflavin and blue light of 200 mW/cm$^2$ the bundle structures loosen further and the collagen bundles appear strongly contorted. The inter-bundle and inter-fibril space increases (arrow heads) and many collagen fibrils appear separated. Scale bar in D is valid for A-D.

Figure 16:
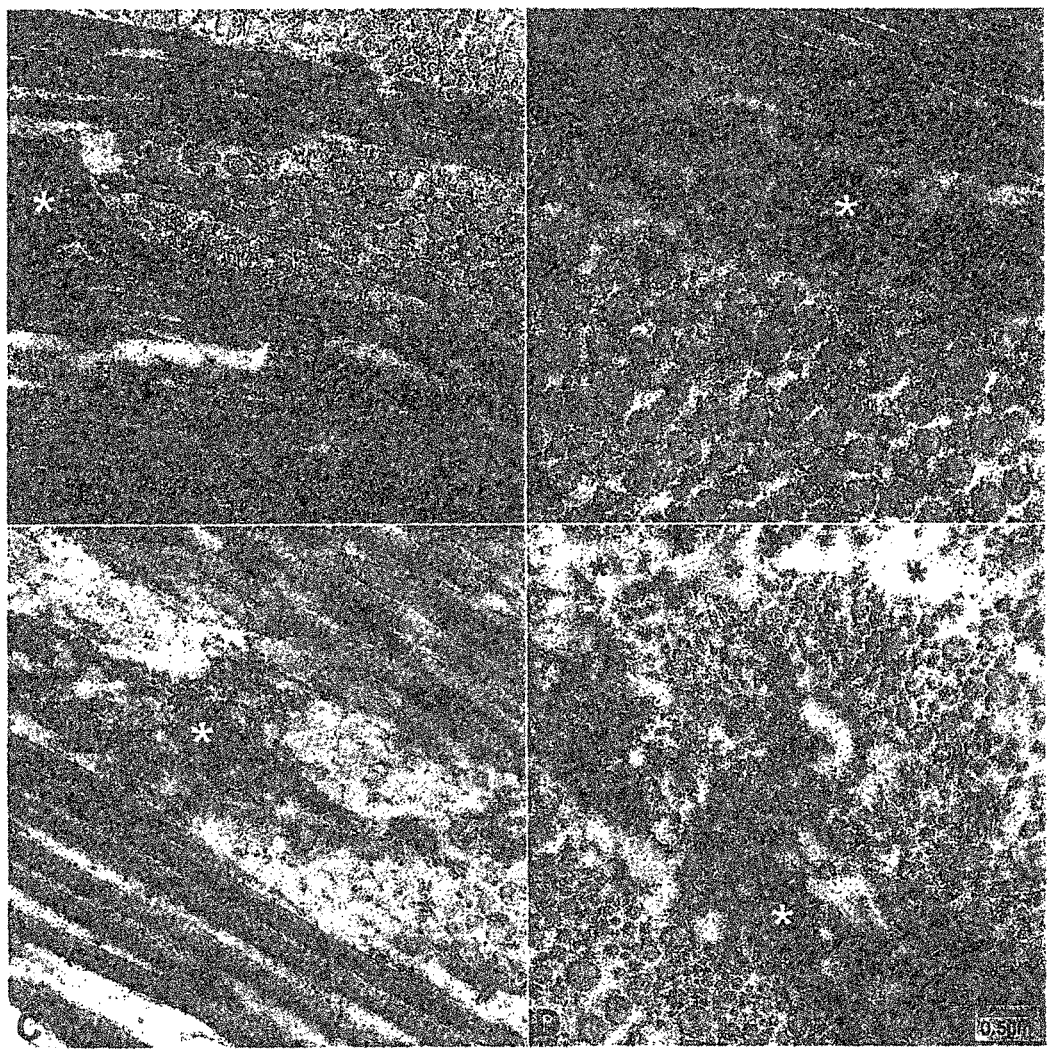
FIG. 16 shows electron microscopic microphotographs of acute isolated (A) and frozen/thawed (B-D) scleral tissue with (C and D) and without (A and B) crosslinking treatment.
Figure 17A:
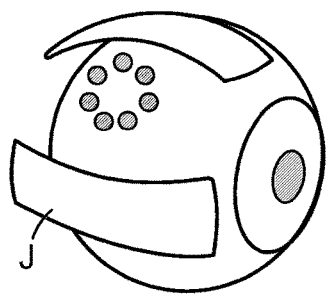
FIGS. 17A-G show various treatment patterns obtainable with the devices according to the present invention.
Figure 17B:
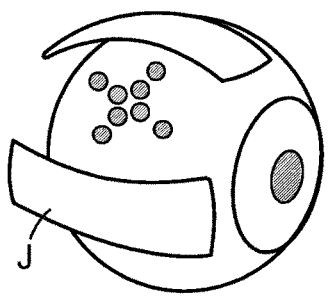
Figure 17C:
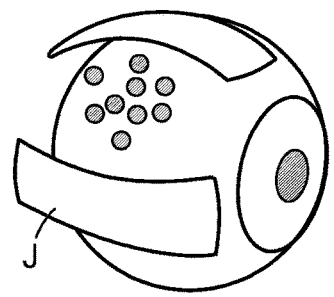
Figure 17D:
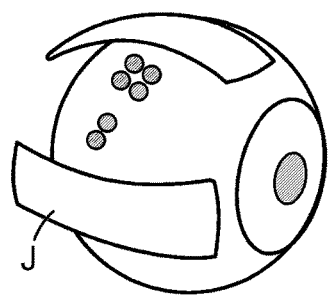
Figure 17E:
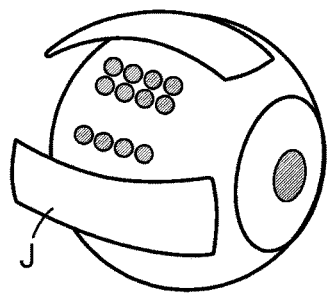
Figure 17F:
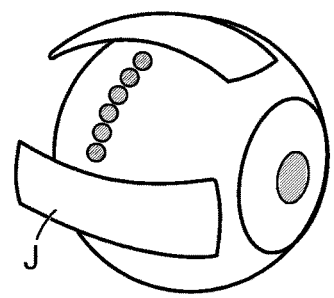
Figure 17G:
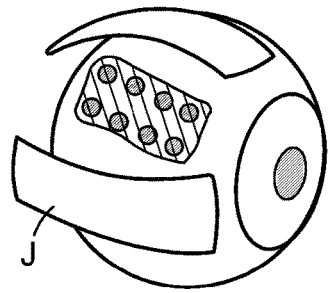

FIG. 16: Electron microscopic microphotographs of acute isolated (A) and frozen/thawed (B-D) scleral tissue with (C and D) and without (A and B) crosslinking treatment. A: Acute isolated non-treated scleral tissue is characterized by a very compact collagen bundle arrangement with different orientations (cross and transverse sections of the bundles are visible). Spindle-like electron dense cell bodies of fibroblasts (asterisk) with tiny cell processes are located between the collagen bundles and sub-cellular structures are well defined and intact. B: As a consequence of storage at −20° C. and thawing fibroblasts (asterisk) of the scleral tissue are swollen and show disrupted cellular structures and cell membranes. Collagen fibrils seem to be intact and are often still organized compactly in bundles. C: After crosslinking treatment with riboflavin and 25 mW/cm$^2$ scleral fibroblasts show similar disrupted appearance as in untreated thawed tissue shown in B. The collagen fibre structure itself appears intact. D: After crosslinking treatment with riboflavin and blue light of 200 mW/cm$^2$ the collagen bundle structures appear slightly loosened and the few collagen fibril arrangements appear disrupted (arrow heads). Occasionally, the inter-fibril space increases (black asterisks) and cellular structures (white asterisk) appear destroyed. Scale bar in D is valid for A-D.

The invention claimed is:

1. A device for a medical treatment of a sclera, the device comprising a single applicator connected to a shaft, wherein:
the applicator is configured to be placed into the Tenon's space;
the applicator has a first surface, wherein the first surface of the applicator is superficially contactable to the surface of an area of the sclera so as to superficially cover said area; and
the applicator comprises a single optical outlet having a distal surface the single optical outlet connected to a single optical guiding element extending from a proximal end of the shaft to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation;
wherein the distal surface of the optical outlet is at least partially coloured for generating heat.

2. The device of claim 1, wherein the applicator comprises a plurality of individual optical outlets, each having a distal surface, the plurality of individual optical outlets being connected to the single optical guiding element.

3. The device of claim 2, wherein the distal surface of at least one of the optical outlets is configured for transmitting light.

4. The device of claim 2, wherein the optical outlets are regularly, irregularly or distinct distributed with respect to the first surface of the applicator, and the first surface of the applicator is preferably virtually subdivided into different areas having different distributions of the optical outlets.

5. The device of claim 4, wherein the density of the optical outlets vary with respect to the first surface of the applicator.

6. The device of claim 2, wherein the applicator has a symmetric shape, and the optical outlets are arranged symmetrically in accordance with the symmetry of the applicator.

7. The device of claim 1, wherein the applicator comprises a single agent channel extending from a proximal end of the shaft to a distal channel opening at the surface of the applicator, the proximal end of the agent channel being connectable to an agent supply.

8. The device of claim 7, wherein the single agent channel extends from a proximal end of the shaft to at least two distal channel openings at the first surface of the applicator.

9. The device of claim 7, wherein the applicator further comprises a channel for sucking away superfluous agent.

10. The device of claim 1, wherein the applicator comprises a plurality of agent channels.

11. The device of claim 10, wherein each agent channel extends from a proximal end of the shaft to at least two distal channel openings at the first surface of the applicator.

12. The device of claim 10, wherein one or more agent channels are for the application of an agent such as riboflavin, whereas one or more of the remaining channels are for sucking away superfluous agent.

13. The device of claim 8, wherein the agent channel(s) is/are at least partly isolated against electromagnetic radiation, preferably isolated against electromagnetic radiation with a wavelength in the range between 100 nm and 2000 nm, and most preferably isolated against electromagnetic radiation with a wavelength in the range between 300 nm and 800 nm.

14. The device of claim 8, wherein the surface of the applicator has a structure adapted to allow for an improved distribution of agent when agent is lead through the agent channel.

15. The device of claim 14, wherein the surface structure comprises chamfers, or elements such as bars, half-spheres, pyramids or cones.

16. The device of claim 1, the optical guiding element being configured for guiding electromagnetic waves configured for crosslinking sclera tissue towards the optical outlet.

17. The device of claim 16, wherein the applicator comprises a plurality of individual optical surface areas connected to the optical guiding element.

18. The device of claim 1, wherein the applicator comprises a plurality of individual first optical surface areas connected to a first optical guiding element and a plurality of individual second optical surface areas connected to a second optical guiding element, the first and second optical guiding element extending from a proximal end of the shaft to the respective distal optical surface areas at the first surface of the applicator, the first optical guiding element being configured for guiding electromagnetic waves towards the optical first optical surface areas, and the second guiding element being associated with a photosensitizer.

19. The device of claim 1, wherein the applicator further comprises a single monopolar or bipolar electrode connected to a single electrical conductor element extending from a proximal end of the shaft to the electrode at the first surface of the applicator.

20. The device of claim 1, wherein the applicator further comprises multiple monopolar or bipolar electrodes connected to multiple electrical conductor elements extending from a proximal end of the shaft to the electrodes at the first surface of the applicator.

21. The device of claim 19, wherein the electrodes provide electrical protein coagulation at a spot.

22. The device of claim 1, further comprising a shield element sized and shaped to at least partially cover the cornea during use of the device.

23. The device of claim 1, further comprising one or more recesses formed in the edge of the applicator, wherein the one or more recesses may be positioned and formed such that the recesses leave free space for eye muscles, blood vessels and/or nerves when the applicator is positioned on said area of the sclera.

24. The device of claim 1, wherein the applicator comprises a base layer made from a material being at least one of sterilisable and heat-resistant.

25. The device of claim 1, wherein the applicator comprises one or more additional layers, wherein the base layer and the one or more additional layers are arranged as stacked layers with the base layer on the outer side of the applicator so as to support the additional layers, and wherein each of the one or more additional layers is preferably made from a plastic or a metal material, more preferably light-diffusing, light blocking and/or sponge like material.

26. The device of claim 25, wherein at least one of the additional layers is a diffuser adapted for diffusing electromagnetic waves, and wherein at least part of the distal openings are arranged within or at the outer side of the additional layer(s) being a diffuser.

27. The device of claim 1, wherein the applicator comprises a base layer made from a material that is impervious to light.

28. A device for a medical treatment of a sclera, the device comprising two, three, four or more applicators each connected to a respective shaft, wherein:
  each applicator is configured to be placed into the Tenon's space;
  each applicator has a first surface, wherein the first surface of the applicator is superficially contactable to the surface of an area of the sclera so as to superficially cover said area;
  each applicator comprises a single optical outlet having a distal surface, the single optical outlet connected to a single optical guiding element extending from a proximal end of the respective shall to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation; and
  wherein the shafts of the applicators are proximally connected to a single proximal shaft;
  wherein the distal surface of the optical outlet is at least partially coloured for generating heat.

29. The device of claim 28, wherein each applicator comprises a plurality of individual optical outlets, each having a distal surface, the plurality of individual optical outlets being connected to the single optical guiding element.

30. The device of claim 29, wherein the distal surface of at least one of the optical outlets is configured for transmitting light.

31. The device of claim 29, wherein the optical outlets are regularly, irregularly or distinctly distributed with respect to the first surface of the applicator, and the first surface of the applicator is virtually subdivided into different areas having different distributions of the optical outlets.

32. The device of claim 31, wherein the density of the optical outlets vary with respect to the first surface of the applicator.

33. The device of claim 29, wherein the applicator has a symmetric shape, and the optical outlets are arranged symmetrically in accordance with the symmetry of the applicator.

34. The device of claim 28, wherein each applicator further comprises a single agent channel extending from a proximal end of the shaft to a distal channel opening at the surface of the applicator, the proximal end of the agent channel being connectable to an agent supply.

35. The device of claim 34, wherein the single agent channel extends from a proximal end of the shaft to at least two distal channel openings at the first surface of the applicator.

36. The device of claim 35, wherein the agent channel(s) is/are isolated against electromagnetic radiation with a wavelength in the range between 100 nm and 2000 nm.

37. The device of claim 33, wherein each applicator further comprises a channel for sucking away superfluous agent.

38. The device of claim 28, wherein each applicator comprises a plurality of agent channels.

39. The device of claim 38, wherein each agent channel extends from a proximal end of the shaft to at least two distal channel openings at the first surface of the applicator.

40. The device of claim 38, wherein one or more agent channels are for the application of an agent such as riboflavin, wherein one or more of the remaining channels are for sucking away superfluous agent.

41. The device of claim 35, wherein the agent channel(s) is/are at least partly isolated against electromagnetic radiation.

42. The device of claim 35, wherein the surface of each applicator has a structure adapted to allow for an improved distribution of agent when agent is lead through the agent channel.

43. The device of claim 42, wherein the surface structure comprises chamfers, or elements such as bars, half-spheres, pyramids or cones.

44. The device of claim 28, the optical guiding element being configured for guiding electromagnetic waves configured for crosslinking sclera tissue towards the optical outlet.

45. The device of claim 44, wherein each applicator comprises a plurality of individual optical surface areas connected to the optical guiding element.

46. The device of claim 28, wherein each applicator comprises a plurality of individual first optical surface areas connected to a first optical guiding element and a plurality of individual second optical surface areas connected to a second optical guiding element, the first and second optical guiding element extending from a proximal end of the shaft to the respective distal optical surface areas at the first surface of the applicator, the first optical guiding element being configured for guiding electromagnetic waves towards the optical first optical surface areas, and the second guiding element being associated with a photosensitizer.

47. The device of claim 28, wherein each applicator further comprises a single monopolar or bipolar electrode connected to a single electrical conductor element extending from a proximal end of the shaft to the electrode at the first surface of the applicator.

48. The device of claim 28, wherein each applicator further comprises multiple monopolar or bipolar electrodes connected to multiple electrical conductor elements extending from a proximal end of the shaft to the electrodes at the first surface of the applicator.

49. The device of claim 47, wherein the electrodes provide electrical protein coagulation at a spot.

50. A method of treating the sclera in a subject comprising the steps of
  (i) placing of the applicator of the device of claim 1 into the Tenon's space in the eye of the subject so that the first surface of the applicator is superficially in contact with a surface of an area of the sclera,
  (ii) applying electromagnetic radiation to the sclera of the subject of a wavelength adapted for thermal treatment of the sclera by protein coagulation.

51. The method of claim 50, comprising the step of applying riboflavin to the sclera for crosslinking.

52. The method of claim 50, comprising applying electrical protein coagulation at a spot.

53. A device for a medical treatment of a sclera, the device comprising a single applicator connected to a shaft, wherein:

the applicator is configured to be placed into the Tenon's space;

the applicator has a first surface, wherein the first surface of the applicator is superficially contactable to the surface of an area of the sclera so as to superficially cover said area; and the applicator comprises a single optical outlet having a distal surface, the single optical outlet connected to a single optical guiding element extending from a proximal end of the shaft to the single distal optical outlet at the first surface of the applicator, the optical guiding element being configured for guiding electromagnetic waves towards the optical outlet, wherein the optical guiding element is configured to guide electromagnetic waves of a wavelength adapted for thermal treatment of the sclera by protein coagulation; wherein the applicator further comprises a single monopolar or bipolar electrode connected to a single electrical conductor element extending from a proximal end of the shaft to the electrode at the first surface of the applicator.

54. The device of claim 53, further comprising at least one additional applicator, each additional applicator being connected to a respective shaft, wherein each additional applicator is configured to be placed into the Tenon's space;

each additional applicator has a first surface, wherein the first surface of the additional applicator is superficially contactable to the surface of an area of the sclera so as to superficially cover said area;

each additional applicator comprises a single optical outlet having a distal surface, the single optical outlet connected to a single optical guiding element extending from a proximal end of the respective shaft to the single distal optical outlet at the first surface of the additional applicator, the optical guiding element being configured for guiding electromagnetic waves towards the optical outlet, wherein the optical guiding element is configured to guide electromagnetic waves of a wavelength adapted for thermal treatment of the sclera by protein coagulation;

wherein each additional applicator further comprises a single monopolar or bipolar electrode connected to a single electrical conductor element extending from a proximal end of the shaft to the electrode at the first surface of each additional applicator; and wherein the shafts of the single applicator and of each additional applicator are proximally connected to a single proximal shaft.

* * * * *

UNITED STATES PATENT AND TRADEMARK OFFICE
CERTIFICATE OF CORRECTION

PATENT NO.         : 10,426,663 B2
APPLICATION NO.    : 15/302854
DATED              : October 1, 2019
INVENTOR(S)        : Hans Peter Iseli, Mike Francke and Peter Wiedemann Page 1 of 1

It is certified that error appears in the above-identified patent and that said Letters Patent is hereby corrected as shown below:

On the Title Page

Item (73) Assignee:
"UNIVERSITÄT LEIPZIG, Leipzig, (DE)",
Should be:
Hans Peter ISELI, Geroldswil, (CH); UNIVERSITÄT LEIPZIG, Leipzig, (DE), Signed and Sealed this
Fourth Day of August, 2020

Andrei Iancu
*Director of the United States Patent and Trademark Office*